United States Patent
Kasahara et al.

(10) Patent No.: US 9,615,798 B2
(45) Date of Patent: Apr. 11, 2017

(54) BIOLOGICAL INFORMATION PROCESSING APPARATUS, AND BIOLOGICAL INFORMATION PROCESSING METHOD

(71) Applicant: SEIKO EPSON CORPORATION, Tokyo (JP)

(72) Inventors: Hirokazu Kasahara, Okaya (JP); Kazuhiro Nishida, Matsumoto (JP); Kimitake Mizobe, Pittsburgh, PA (US)

(73) Assignee: SEIKO EPSON CORPORATION, Tokyo (JP)

( * ) Notice: Subject to any disclaimer, the term of this patent is extended or adjusted under 35 U.S.C. 154(b) by 98 days.

(21) Appl. No.: 14/610,453

(22) Filed: Jan. 30, 2015

(65) Prior Publication Data
US 2015/0216484 A1   Aug. 6, 2015

(30) Foreign Application Priority Data

Jan. 31, 2014   (JP) .................. 2014-017022

(51) Int. Cl.
*A61B 5/00* (2006.01)
*A61B 5/02* (2006.01)
(Continued)

(52) U.S. Cl.
CPC .......... *A61B 5/7285* (2013.01); *A61B 5/0205* (2013.01); *A61B 5/1118* (2013.01);
(Continued)

(58) Field of Classification Search
CPC ... A61B 5/7285; A61B 5/0205; A61B 5/1118; A61B 5/1123; A61B 5/14532;
(Continued)

(56) References Cited

U.S. PATENT DOCUMENTS 7,280,860 B2   10/2007   Ikeda et al.
2004/0034293 A1*   2/2004   Kimball ............. A61B 5/14551
                                                    600/323
(Continued)

FOREIGN PATENT DOCUMENTS

JP   2006-247375 A   9/2006
JP   4236950 B2      3/2009
(Continued)

OTHER PUBLICATIONS

Jun. 19, 2015 Search Report issued in European Patent Application No. 15153021.9.

*Primary Examiner* — Carl H Layno
*Assistant Examiner* — Erin M Piateski
(74) *Attorney, Agent, or Firm* — Oliff PLC

(57) ABSTRACT

In a biological information processing apparatus, a body motion detection unit detects a body motion of a subject. A measurement method selection unit selects one measurement method on the basis of a detection result from the body motion detection unit, from among a plurality of measurement methods of measuring a blood glucose level by applying irradiation waves toward a living body of the subject. A measurement result display control unit performs control for displaying a measurement result which is obtained by performing a measurement according to the one measurement method.

8 Claims, 18 Drawing Sheets

(51) Int. Cl.
*A61B 5/0205* (2006.01)
*A61B 5/11* (2006.01)
*A61B 5/145* (2006.01)
*A61B 5/1455* (2006.01)

(52) U.S. Cl.
CPC .......... *A61B 5/1123* (2013.01); *A61B 5/1455* (2013.01); *A61B 5/14532* (2013.01); *A61B 5/489* (2013.01); *A61B 5/02007* (2013.01); *A61B 5/681* (2013.01); *A61B 5/721* (2013.01); *A61B 5/742* (2013.01); *A61B 2562/0238* (2013.01); *A61B 2562/0242* (2013.01)

(58) Field of Classification Search
CPC ... A61B 5/1455; A61B 5/489; A61B 5/02007; A61B 5/681; A61B 5/721; A61B 5/742
USPC ........................................................ 600/301
See application file for complete search history.

(56) References Cited

U.S. PATENT DOCUMENTS

| | | | | |
|---|---|---|---|---|
| 2007/0093698 | A1* | 4/2007 | Goldberger | A61B 5/0095 600/310 |
| 2014/0018645 | A1* | 1/2014 | Wada | A61B 5/0095 600/316 |

FOREIGN PATENT DOCUMENTS

| | | |
|---|---|---|
| JP | 2012-200271 A | 10/2012 |
| JP | 2014-124453 A | 7/2014 |
| JP | 2014-124454 A | 7/2014 |
| JP | 2014-124455 A | 7/2014 |
| WO | 2004/016170 A1 | 2/2004 |
| WO | 2007/063435 A2 | 6/2007 |
| WO | 2009/008933 A2 | 1/2009 |
| WO | 2012/137855 A1 | 10/2012 |

* cited by examiner

| MEASUREMENT POINT NUMBER | FOR BLOOD VESSEL TYPE | | FOR NON-BLOOD VESSEL TYPE | |
|---|---|---|---|---|
| | IRRADIATION POSITION (MEASUREMENT LIGHT EMITTING ELEMENT) | MEASUREMENT LIGHT RECEPTION POSITION (MEASUREMENT LIGHT RECEIVING ELEMENT) | IRRADIATION POSITION (MEASUREMENT LIGHT EMITTING ELEMENT) | MEASUREMENT LIGHT RECEPTION POSITION (MEASUREMENT LIGHT RECEIVING ELEMENT) |
| A_001 | xxxxx | xxxxx | xxxxx | xxxxx |
| A_002 | xxxxx | xxxxx | xxxxx | xxxxx |
| ... | ... | ... | ... | ... |

FIG.10

| VARIANCE VALUE OF DETECTED ACCELERATION | MEASUREMENT TIME |
|---|---|
| BELOW PREDETERMINED THRESHOLD VALUE (LEVEL OF BODY MOTION : LOW) | T11 |
| PREDETERMINED THRESHOLD VALUE OR GREATER (LEVEL OF BODY MOTION : HIGH) | T13 |

| VARIANCE VALUE OF DETECTED ACCELERATION | NUMBER OF MEASUREMENT POINTS |
|---|---|
| D11~D13 | 4 |
| D13~D15 | 8 |
| D15~D17 | 12 |
| D17~D19 | 16 |

| MEASUREMENT POINT CANDIDATE NUMBER | IRRADIATION POSITION (MEASUREMENT LIGHT EMITTING ELEMENT) | MEASUREMENT LIGHT RECEPTION POSITION (MEASUREMENT LIGHT RECEIVING ELEMENT) | PRIORITY FLAG |
|---|---|---|---|
| B_001 | xxxxx | xxxxx | OFF |
| B_002 | xxxxx | xxxxx | OFF |
| B_003 | xxxxx | xxxxx | ON |
| B_004 | xxxxx | xxxxx | OFF |
| ⋮ | ⋮ | ⋮ | ⋮ |

FIG.20

BIOLOGICAL INFORMATION PROCESSING APPARATUS, AND BIOLOGICAL INFORMATION PROCESSING METHOD

The present application claims priority to Japanese Patent Application JP 2014-017022, filed Jan. 31, 2014, the entire disclosure of which is hereby incorporated by reference.

BACKGROUND

1. Technical Field

The present invention relates to a biological information processing apparatus and the like. The apparatus may process biological information of a subject.

2. Related Art

In the related art, as a measurement apparatus that measures biological information of a subject, there is a measurement apparatus in which a sensor or the like is in contact with a skin surface of a subject, and measurement light is applied toward a living body of the subject, so that a blood component is measured. As such a biological information measurement apparatus, there is an apparatus which effectively uses a measurement result which is obtained by an external apparatus with a specification different from a dedicated specification, and can thus selectively display a highly accurate measurement result.

JP-A-2006-247375 is an example of the related art. However, in a case where a sensor or the like is in contact with the skin surface of the subject and a measurement is performed, a target may be deviated due to a body motion of the subject and thus measurement accuracy may be considerably reduced, or a measurement cannot be performed so that an effective measurement result may not be obtained. Thus, a measurement result may not be stably provided. Particularly, in a case of measuring biological information essential for healthcare or life, for example, in a case of measuring a blood glucose level of a diabetic, since a reduction in the blood glucose level may directly lead to a crisis, the blood glucose level is required to be continuously monitored, and a stable measurement result is required to be supplied.

SUMMARY

An advantage of some aspects of the invention is to stably provide a measurement result.

A first aspect of the invention is directed to a biological information processing apparatus including a body motion detection unit that detects a body motion of a subject; a selection unit that selects one measurement method on the basis of a detection result from the body motion detection unit, from among a plurality of measurement methods of measuring a predetermined component in blood by applying irradiation waves toward a living body of the subject; and a display control unit that performs control for displaying a measurement result which is obtained by performing a measurement according to the one measurement method.

As another aspect of the invention, the first aspect of the invention may be configured as a biological information processing method including detecting a body motion of a subject; selecting one measurement method on the basis of a result of the detection, from among a plurality of measurement methods of measuring a predetermined component in blood by applying irradiation waves toward a living body of the subject; and performing control for displaying a measurement result which is obtained by performing a measurement according to the one measurement method.

According to the first aspect and another aspect, when irradiation waves are applied to a living body of a subject and a predetermined component in blood is measured, a body motion of the subject can be detected, one measurement method can be selected on the basis of a detection result from among a plurality of measurement methods, and display of a measurement result according to the selected measurement method can be controlled. Therefore, it is possible to display a measurement result according to one measurement method suitable for a detection result of a body motion, and thus to stably provide a measurement result.

A second aspect of the invention is directed to the biological information processing apparatus according to the first aspect, which further includes a parameter setting unit that sets a measurement parameter related to the one measurement method on the basis of the detection result.

A third aspect of the invention is directed to the biological information processing apparatus according to the second aspect, wherein the parameter setting unit sets at least one of the number of measurement points, and a measurement time related to duration in which the irradiation waves are applied, as the measurement parameter.

According to the second aspect, it is possible to set a measurement parameter according to selected one measurement method on the basis of a detection result of a body motion. In addition, according to the third aspect, it is possible to set at least one of the number of measurement points and a measurement time as the measurement parameter.

A fourth aspect of the invention is directed to the biological information processing apparatus according to any one of the first to third aspects, wherein the selection unit selects one measurement method from among a plurality of measurement methods which are different depending on measurement object sites.

According to the fourth aspect, when one measurement method is selected, it is possible to select a measurement method according to a measurement object site.

A fifth aspect of the invention is directed to the biological information processing apparatus according to the fourth aspect, wherein the selection unit selects one measurement method in which a blood vessel portion is set as the measurement object site in a case where the detection result satisfies a condition indicating that a level of the body motion is low. A sixth aspect of the invention is directed to the biological information processing apparatus according to the fourth or fifth aspect, wherein the selection unit selects one measurement method in which a non-blood vessel portion other than a blood vessel is set as the measurement object site in a case where the detection result satisfies a condition indicating that a level of the body motion is high.

According to the fifth aspect, if a level of a body motion is low, it is possible to select a measurement method in which a blood vessel portion is set as a measurement object site. According to the sixth aspect, if a level of the body motion is high, it is possible to select a measurement method in which a non-blood vessel portion other than a blood vessel is set as a measurement object site.

A seventh aspect of the invention is directed to the biological information processing apparatus according to the first aspect, wherein the biological information processing apparatus further includes a measurement unit that measures the component by using the plurality of measurement methods together, and the display control unit displays a measurement result which is obtained by performing a measurement according to the one measurement method among measurement results from the measurement unit.

According to the seventh aspect, measurements according to a plurality of measurement methods can be performed together, and a measurement result can be selectively displayed on the basis of a detection result of a body motion.

An eighth aspect of the invention is directed to the biological information processing apparatus according to any one of the first to seventh aspects, wherein the measurement methods is a plurality of methods for measuring a blood glucose level. According to the eighth aspect, it is possible to measure a blood glucose level as a component in extracellular fluid.

BRIEF DESCRIPTION OF THE DRAWINGS

The invention will be described with reference to the accompanying drawings, wherein like numbers reference like elements.

FIG. 10 is a diagram illustrating a data configuration example of an irradiation/light reception position list.

FIG. 15 is a data configuration example of a parameter setting table in the third embodiment.

FIG. 19 is a data configuration example of a parameter setting table in a fourth embodiment.

FIG. 20 is a diagram illustrating a data configuration example of a measurement point candidate list.

DESCRIPTION OF EXEMPLARY EMBODIMENTS

Figure 1:
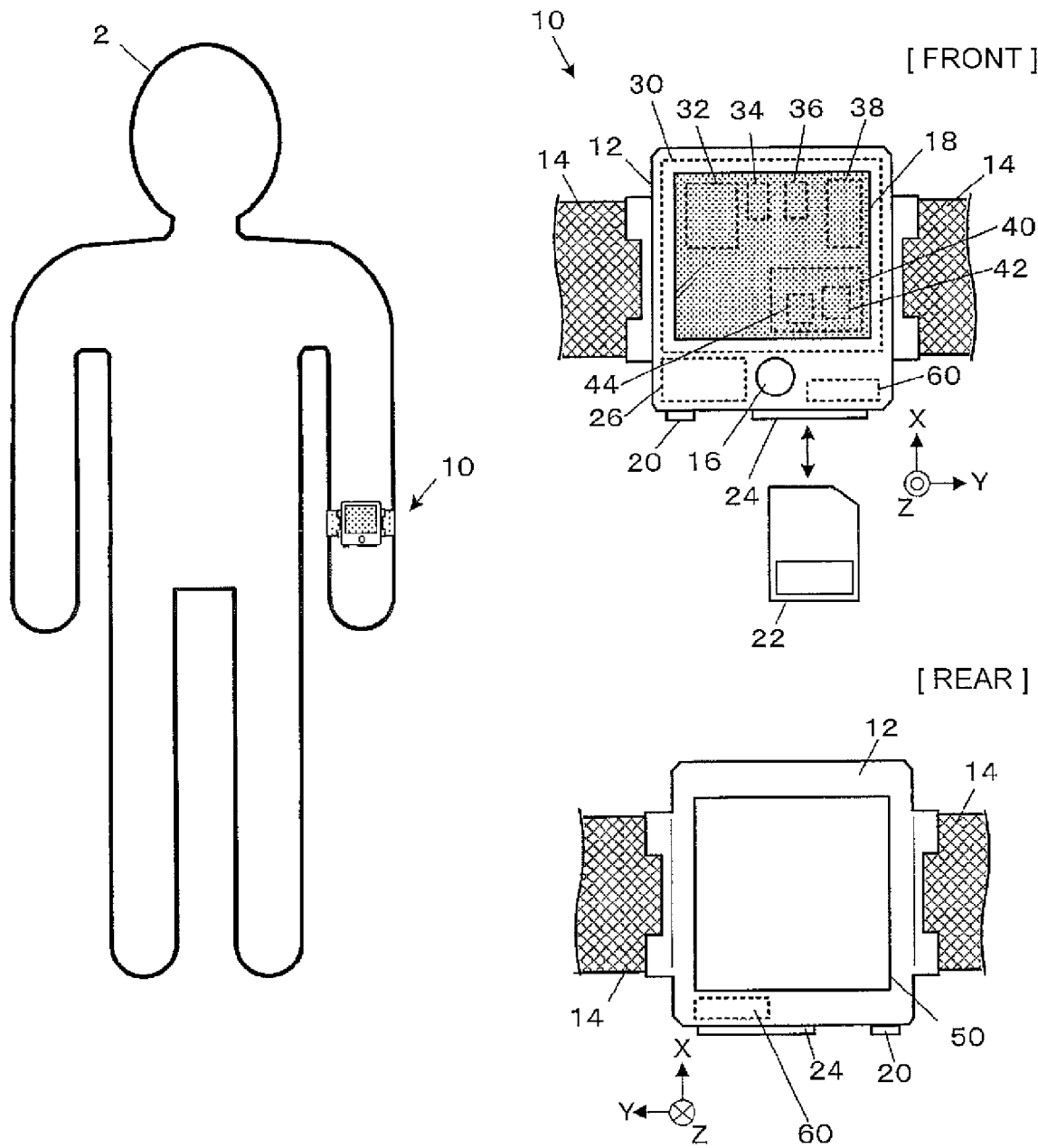
FIG. 1 is an exterior view illustrating an entire configuration example of a biological information processing apparatus.

Hereinafter, with reference to the drawings, a biological information processing apparatus and a biological information processing method according to embodiments of the invention will be described. In addition, the invention is not limited by the embodiments described below, and an applicable form of the invention is not limited to the following embodiments. Throughout the drawings, the same reference numerals are given to the same constituent elements.

First Embodiment

In a first embodiment, different measurement methods are selectively employed in a switching manner so that a so-called "blood glucose level" is measured as a predetermined component in blood. The different measurement methods includes a "blood vessel type" measurement in which a blood vessel is used as a measurement object site, and a glucose concentration in blood is measured so that a blood glucose level is obtained, and a "non-blood vessel type" measurement in which a biological tissue portion (hereinafter, referred to as a "non-blood vessel part") which is a non-blood vessel portion other than the blood vessel is used as a measurement object site, and a glucose concentration in tissue fluid is measured so that a blood glucose level is obtained. It can be said that the first embodiment is an embodiment in which a measurement method is defined with a measurement object site as a reference, and a measurement in which a measurement object site is different is regarded as a different measurement method.

In the "blood vessel type" in which a measurement object site is a blood vessel, a blood glucose level can be measured with high accuracy. On the other hand, since a region of the blood vessel is narrow, a blood vessel position acquired by capturing a biological image in advance tends not to match a blood vessel position in an actual measurement. As a factor thereof, there may be a case where a mounting location of a sensor module 50 described later is deviated due to a body motion of a subject 2, or a case where a blood vessel moves due to a body motion. In such a case, a blood vessel is deviated from a measurement target, and thus measurement accuracy is considerably reduced. Therefore, there is disadvantageous in that a measurement result may not be stably provided in the "blood vessel type" measurement.

In contrast, in the "non-blood vessel type" in which a measurement target site is a non-blood vessel part, a rapid change in a blood glucose level is hardly detected compared with the "blood vessel type", and accordingly measurement accuracy is reduced, but a region of the non-blood vessel part (specifically, a dermal layer) is wide, and thus the non-blood vessel part is scarcely deviated from a measurement target unlike in the "blood vessel type" even if a mounting location of the sensor module 50 is deviated. For this reason, there is advantageous in that a measurement can be performed with stable accuracy in the "non-blood vessel type" measurement.

Entire Configuration

FIG. 1 is an exterior view illustrating an entire configuration example of a non-invasive biological information processing apparatus 10 in the first embodiment. The biological information processing apparatus 10 functions as a measurement apparatus which measures a component of body fluid such as blood or tissue fluid of the subject 2, and a data logger which stores measured data, and can be said to be a kind of computer. As illustrated in FIG. 1, the biological information processing apparatus 10 is constituted by, for example, a wrist watch type wearable apparatus, and is mounted on a body part such as the arm, the leg, the neck, or the like of the subject 2 with a band 14 provided in a main body case 12, so as to be used.

The biological information processing apparatus 10 is provided with an operation switch 16 and a touch panel 18 which is also used as an image display unit on a front surface (a surface directed outwards when the subject 2 wears the biological information processing apparatus 10) of the main body case 12 as an operation input unit. The subject 2 who is a user can input various operations such as a measurement start operation by using the switch and panel.

A communication device 20 in which a wired cable for communication with external devices is attachable and detachable, and a reader/writer 24 which performs reading and writing data from and to a memory card 22 are provided on a side surface of the main body case 12. In addition, the sensor module 50 as a main sensor which applies measurement light toward a living body of the subject 2 as irradiation waves and receives reflected wave light, and an acceleration sensor 60 which is disposed to be adjacent to the sensor module 50, are provided on a rear surface (a surface which comes into contact with the skin of the subject 2 when the subject 2 wears the biological information processing apparatus 10) side of the main body case 12. A charging type internal battery 26 and a control board 30 are built into the main body case 12.

In a configuration in which communication with an external device is performed in a wireless manner, the communication device 20 is implemented by a wireless communication module and an antenna.

The memory card 22 is a data rewritable nonvolatile memory which is attachable and detachable. As the memory card 22, not only a flash memory, but also a rewritable nonvolatile memory such as a ferroelectric random access memory (FeRAM) or a magnetoresistive random access memory (MRAM) may be used.

A type of charging the internal battery 26 may be set as appropriate. For example, there may be a configuration in which an electric contact is separately provided on the rear surface side of the main body case 12, the main body case 12 is set in a cradle connected to a domestic power supply, and the battery 26 is conducted and charged via the electric contact and the cradle, or the battery 26 may be charged in a non-contact manner.

The acceleration sensor 60 detects an acceleration vector of the subject 2. For example, the biological information processing apparatus 10 uses an X axis component and a Y axis component as components of detection acceleration among detection axes of an X axis, a Y axis, and a Z axis of the acceleration sensor 60 illustrated near the main body case 12 of FIG. 1, and detects a displacement in a front surface direction (XY plane) of the main body case 12 as a body motion of the subject 2.

The control board 30 collectively controls the biological information processing apparatus 10. Specifically, the control board 30 is equipped with a central processing unit (CPU) 32, a main memory 34, a measurement data memory 36, a touch panel controller integrated circuit (IC) 38, and a sensor module controller 40. In addition, the control board 30 may be equipped with an electronic component such as a power supply management IC or an image processing IC as appropriate.

The main memory 34 is a storage medium which can store a program, initial setting data, or a calculation value of the CPU 32. The main memory 34 is implemented by using a RAM, a ROM, a flash memory, or the like as appropriate. The program or the initial setting data may be stored in the memory card 22.

The measurement data memory 36 is a data rewritable nonvolatile memory and is a storage medium which stores measurement data of a blood glucose level. As the measurement data memory 36, not only a flash memory, but also a rewritable nonvolatile memory such as a ferroelectric random access memory (FeRAM) or a magnetoresistive random access memory (MRAM) may be used. The measurement data may be stored in the memory card 22.

The touch panel controller IC 38 is an IC which realizes a driver function for displaying an image on the touch panel 18 and realizes a touch input function. The touch panel controller IC 38 and the touch panel 18 can be implemented by using a well-known technique as appropriate.

The sensor module controller 40 includes an IC or a circuit having a function of causing the sensor module 50 to apply measurement light and an IC or a circuit having a function of causing the sensor module 50 to receive light (transmitted light) which is a result of the measurement light being transmitted through a biological tissue of the subject 2 or light (reflected light) which is a result of the measurement light being reflected in the biological tissue.

More specifically, the sensor module 50 includes a light emission controller 42 constituted by an IC or a circuit which individually controls light emission of a plurality of light emitting elements (elements emitting measurement light through conduction) provided in the sensor module 50, and a light reception controller 44 constituted by an IC or a circuit which controls light reception of a plurality of light receiving elements (elements outputting an electric signal corresponding to an amount of received light due to photoelectric conversion provided in the sensor module 50). The sensor module controller 40 may be constituted by a plurality of ICs. For example, different ICs may be used as an IC or a circuit corresponding to the light emission controller 42 and an IC or a circuit corresponding to the light reception controller 44. Alternatively, some of the functions may be realized by the CPU 32.

Figure 2A:
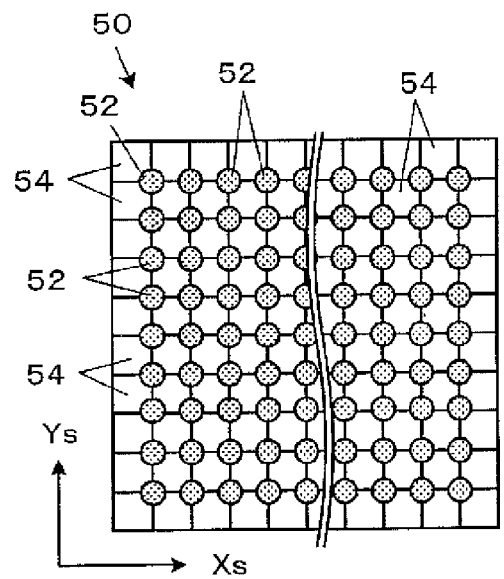
FIGS. 2A and 2B are diagrams illustrating a configuration example of a sensor module.
Figure 2B:
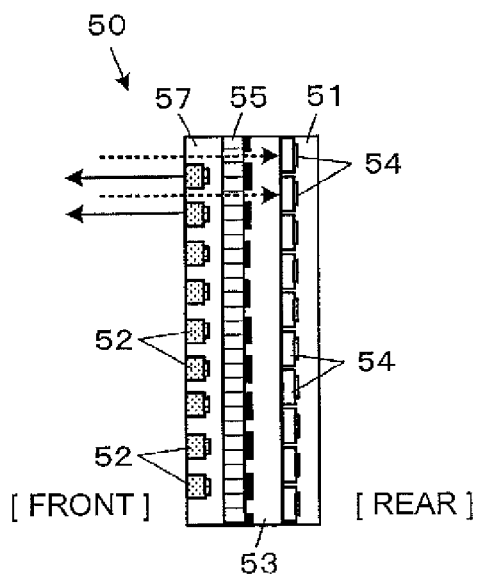

FIGS. 2A and 2B are diagrams illustrating a configuration of the sensor module 50. FIG. 2A is a plan view and FIG. 2B is a cross-sectional view. For better understanding, a light emitting element 52 or a light receiving element 54 is intentionally enlarged and illustrated. A size and an aspect ratio are not limited thereto, and may be set as appropriate. The sensor module 50 is a device formed by laminating a layer in which a plurality of light emitting elements 52 are arranged in a planar shape and a layer in which a plurality of light receiving elements 54 are arranged in a planar shape. In other words, the sensor module 50 is an image sensor with a light source, and is a sensor array which realizes both functions of irradiation and light reception of measurement light. The sensor module 50 may be integrally formed with the sensor module controller 40.

The light emitting elements 52 are an irradiation unit which applies measurement light, and may be implemented by, for example, light emitting diodes (LEDs) or organic light emitting diodes (OLEDs). In a case of measuring a blood glucose level, the light emitting elements 52 employ elements which can emit light including near infrared rays having subcutaneous transparency close to a visible region.

The light receiving elements 54 are imaging elements which receive transmitted light or reflected light of the measurement light and output an electric signal corresponding to a light reception amount. For example, the light receiving elements 54 may be implemented by semiconductor elements such as charge coupled device (CCD) image sensors or complementary metal oxide semiconductor (CMOS) image sensors. A single light receiving element 54 is assumed to include a plurality of elements which receive RGB wavelength components.

The sensor module 50 is a device in which 1) a light receiving layer 51, 2) a light blocking layer 53, 3) a spectroscopic layer 55, and 4) a light emitting layer 57 are laminated in this order from a base side (the front side of the main body case 12). A plurality of light receiving elements 54 are arranged in a planar shape or in a lattice shape in the light receiving layer 51. The light blocking layer 53 selectively blocks light which is not directed to each light receiving element 54, and the spectroscopic layer 55 selectively transmits near infrared rays therethrough. A plurality of light emitting elements 52 are arranged in a planar shape or a lattice shape at positions which are located between adjacent light receiving elements 54 and do not impede optical paths along which light transmitted through or reflected in a biological tissue reaches the light receiving elements 54 in the light emitting layer 57.

The light receiving elements 54 of the light receiving layer 51 are disposed in a matrix in which pixels can be identified with an Xs-Ys orthogonal coordinate system, such as a well-known CCD image sensor. In other words, the sensor module 50 functions in the same manner as the well-known image sensor. A shape, a size, and an arrangement pattern of the light receiving elements 54 may be set as appropriate.

Each of the light emitting elements 52 of the light emitting layer 57 is disposed at butted part of corners of the adjacent light receiving elements 54 when the sensor module 50 is viewed from the front side (the rear side of the main body case 12). More specifically, a single light emitting element 52 is disposed at the butted part of corners of the four light receiving elements 54, and the whole light emitting elements 52 are disposed in a matrix which can be identified with the Xs-Ys orthogonal coordinate system in the same manner as the light receiving elements 54. The sensor module 50 includes a driving mechanism which causes the light emitting elements 52 to selectively emit light, and driving of the light emitting elements 52 can be controlled in the same manner as in an active matrix of a liquid crystal panel display.

A well-known semiconductor micro-processing technique used for manufacturing of a CCD image sensor or an OLED display may be applied as appropriate to manufacturing of the sensor module 50 having such a laminate structure.

A size or an arrangement interval of the light emitting elements 52 and a size or an arrangement interval of the light receiving elements 54 may be set as appropriate. For example, an arrangement interval of 1 to 500 [µm] is preferably used, and, for example, 50 to 200 [µm] may be used from the viewpoint of manufacturing cost and measurement accuracy. In order to narrow an irradiation range of measurement light applied from the light emitting elements 52 or to polarize the measurement light, or in order to accurately correct light transmitted through or reflected in a biological tissue at the light receiving elements 54, a light collecting layer having an optical element may be further provided in the sensor module 50. In addition, a protective layer for preventing a surface damage may be provided as appropriate. The light emitting elements 52 and the light receiving elements 54 are not only laminated but may also be arranged in parallel to each other.

Overview

The biological information processing apparatus 10 is fixed with the band 14 so that the rear surface to which the sensor module 50 is exposed is brought into close contact with the skin of the subject 2. Since the sensor module 50 is brought into close contact with the skin, it is possible to minimize factors which reduce measurement accuracy, such as reflection of measurement light at the skin surface or scattering thereof near the skin surface.

As a measurement procedure of a blood glucose level in the "blood vessel type", first, a blood vessel under the skin of the body covered with the sensor module 50 is selected as a measurement object site. In addition, the selected blood vessel is irradiated with measurement light as a target and light is received. Then, a blood vessel transmitted light component which has been transmitted through the blood vessel is extracted from a light reception result (intensity of received light), and a blood glucose level is calculated on the basis of a relative spectrum (absorption spectrum) which reflects an amount of the blood vessel transmitted light component.

On the other hand, in the "non-blood vessel type", a non-blood vessel part under the skin of the body covered with the sensor module 50 is selected as a measurement object site. In addition, the selected non-blood vessel part is irradiated with measurement light as a target and light is received. Then, a non-blood vessel part transmitted light component which has been transmitted through the non-blood vessel part is extracted from a light reception result, and a blood glucose level is calculated on the basis of an absorption spectrum.

Figure 3:
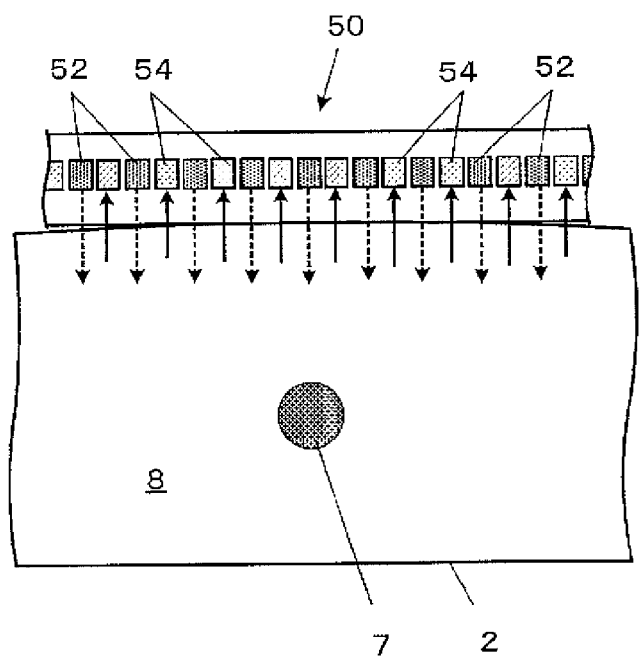
FIG. 3 is a conceptual diagram illustrating a method of acquiring a blood vessel position.

In order to select a blood vessel and a non-blood vessel part as measurement object sites, it is necessary to identify where a blood vessel is present under the skin covered with the sensor module 50. FIG. 3 is a conceptual diagram illustrating a method of acquiring a blood vessel position, and corresponds to a cross-sectional view of a portion of the subject 2 covered with the sensor module 50. The sensor module 50 is simply illustrated.

When a blood vessel position is acquired, first, in the same manner as in vein pattern detection in a well-known vein authentication technique, the light emitting layer 52 of the sensor module 50 are made to simultaneously emit light so as to irradiate the entire location where the sensor module 50 is mounted with measurement light. In addition, light which has been transmitted through or reflected in a biological tissue (subcutaneous tissue) under the skin is collected (an image is captured) by using all the light receiving elements 54, so as to acquire a biological image.

Here, the biological image acquired by the sensor module 50 becomes a set of luminance data of pixels which respectively correspond to the light receiving elements 54 of the sensor module 50, and can be obtained as a two-dimensional image of the Xs-Ys orthogonal coordinate system in the same manner as pixel coordinates of the sensor module 50. The blood vessel more easily absorbs near infrared rays than a location where there is no blood vessel 7, due to an influence of blood which flows therethrough. For this reason, the blood vessel position has lower luminance and is darker than other regions. Therefore, if a region whose luminance is lower is extracted from the biological image, it is possible to identify whether or not a blood vessel is reflected in each pixel, that is, whether or not the blood vessel is present under each of the light receiving elements 54. The term "under the light receiving elements 54" is related to description of an operation performed by the subject 2, and, more accurately, indicates that a blood vessel is located in an opposite direction (a light reception direction) to the light receiving elements 54 with the body surface of the subject 2 interposed therebetween.

Figure 4:
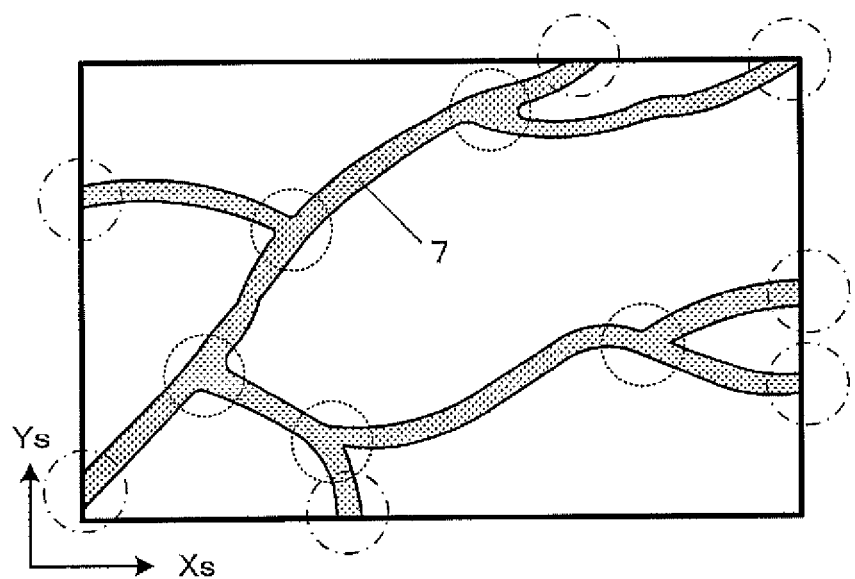
FIG. 4 is a diagram schematically illustrating a biological image.

FIG. 4 is a diagram schematically illustrating a biological image. In an example of FIG. 4, a strip-shaped region hatched with a diagonal or dotted pattern indicates a position of the blood vessel 7. In addition, a method of acquiring a blood vessel position is not limited to the exemplified method. For example, there may be a method in which a relative position of an inner structure of a living body is acquired in advance by using a well-known biological tomographic image measurement technology such as ultrasonic echo, magnetic resonance imaging (MRT), or computed tomography (CT), and a blood vessel position is determined on the basis thereof.

Figure 5:
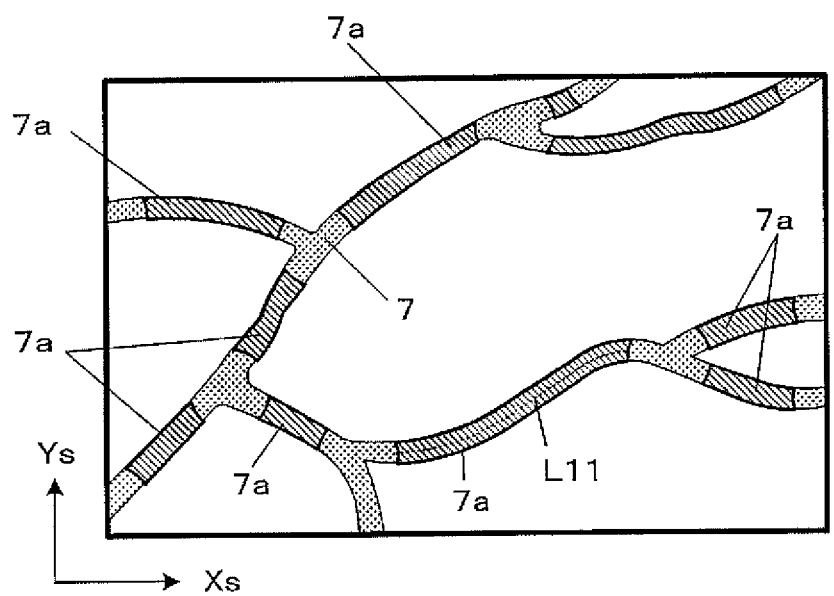
FIG. 5 is a diagram illustrating a blood vessel portion which is obtained by excluding an accuracy reducing factor portion from the blood vessel position of FIG. 4.

If the position of the blood vessel 7 is acquired, a blood vessel portion suitable for the "blood vessel type" measurement is selected. First, blood vessel portions such as a branch point or a joint point of the blood vessel 7 surrounded by a broken line in FIG. 4, and biological image end parts surrounded by dot chain lines are excluded as portions (accuracy reducing factor portions) which may cause accuracy to be reduced. This is because, when measurement light reaches the branch point or the joint point of the blood vessel, transmitted light or reflected light of a non-blood vessel part other than the blood vessel is mixed with light received at a light reception position, and thus the mixed light influences an absorption spectrum of a blood vessel transmitted light which is desired to be originally obtained, so that measurement accuracy is reduced. In addition, the blood vessel portions at the biological image end parts surrounded by the dot chain lines are excluded since there is a possibility that a branch point or a joint point of a blood vessel may be present near the outside the imaging range. FIG. 5 is a diagram illustrating an example of a blood vessel portion 7a obtained by excluding the accuracy reducing factor portions from the blood vessel position of FIG. 4. For example, the diagonally hatched portions are remaining blood vessel portions 7a without being excluded.

Figure 6:
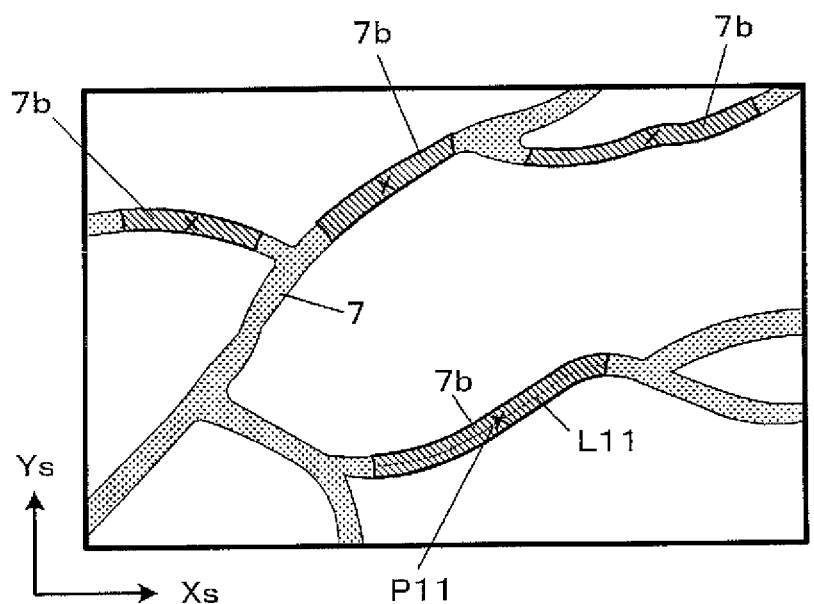
FIG. 6 is a diagram illustrating a blood vessel portion selected on the basis of the smallest site length.

In addition, irradiation light from the light emitting elements 52 are diffused and reflected inside a biological tissue, and some of the reflected light is received by the light receiving elements 54. In other words, some of the light received by the light receiving element 54 becomes blood vessel transmitted light, but as a ratio of the blood vessel transmitted light increases, an absorption spectrum which more remarkably represents a feature of a component in blood may be obtained, and thus measurement accuracy increases. Here, a relatively thin blood vessel is extracted to be thin in a blood vessel pattern specified from a biological image, and is intermittently extracted depending on cases. In addition, an amount of blood vessel transmitted light is small in a blood vessel which is located at a relatively deep position, and may thus be intermittently extracted in the same manner. Therefore, a blood vessel portion having a length which is equal to or larger than a predetermined smallest site length is selected. A length of the blood vessel portion may be, for example, a length of a central line L11, and may be the number of pixels forming the central line L11. FIG. 6 is a diagram illustrating an example of a blood vessel portion 7b which is finally selected. For example, a diagonally hatched blood vessel portion 7b is selected on the basis of the "smallest site length".

If the blood vessel portion 7b suitable for the measurement is selected, in order to be used for the "blood vessel type" measurement, a process (a blood vessel type irradiation/light reception position selection process) of selecting an irradiation position of measurement light (measurement light emitting element) and a measurement light reception position (measurement light receiving element) is performed. In addition, in order to be used for the "non-blood vessel type" measurement, a process (a non-blood vessel type irradiation/light reception position selection process) of selecting an irradiation position of measurement light (measurement light emitting element) and a measurement light reception position (measurement light receiving element) is performed.

Figure 7A:
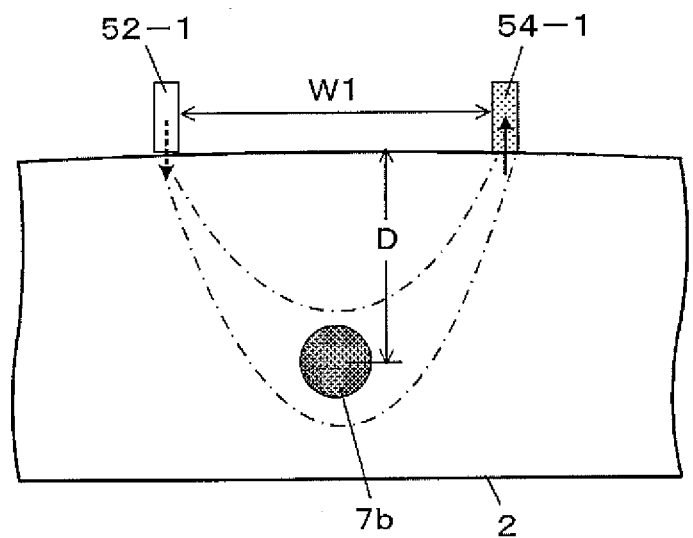
FIGS. 7A and 7B are diagrams illustrating propagation of light in a biological tissue.
Figure 7B:
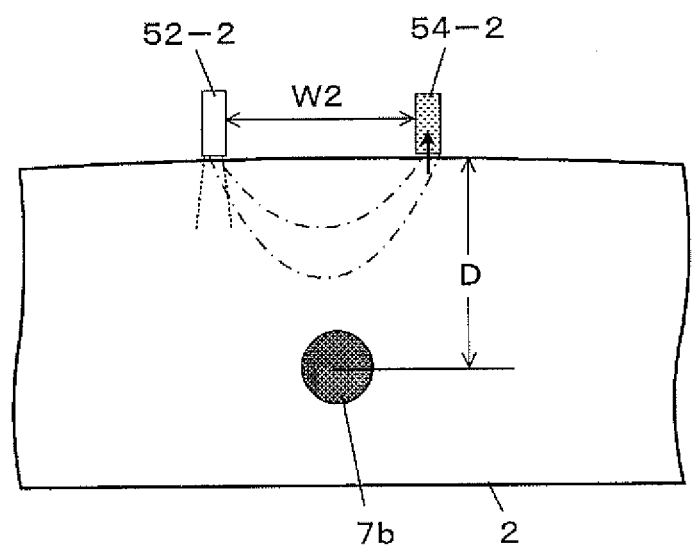

FIGS. 7A and 7B are diagrams for explaining propagation of light in a biological tissue, and are cross-sectional views in a depth direction. Light applied from a certain light emitting element 52 is diffused and reflected inside the biological tissue, and some of the applied light reaches a certain light receiving element 54. A propagation path of the light forms a so-called banana shape (a region interposed between two arcs), and a width in the depth direction is largest in the vicinity of approximately a center thereof. The depth (reachable depth) of the propagation depth is increased as a gap between the light emitting element 52 and the light receiving element 54 becomes larger (FIG. 7A), and the depth is reduced as the gap therebetween becomes smaller (FIG. 7B).

In the "blood vessel type", in order to increase measurement accuracy, it is desirable that a larger amount of blood vessel transmitted light is received by the light receiving element 54. From this factor, the optimum gap (optimum distance) W1 between the light emitting element 52 and the light receiving element 54 illustrated in FIG. 7A may be defined according to an expected depth D of the target blood vessel 7 (a distance from the skin surface to the center of the blood vessel) on the condition that the blood vessel 7 is located at a substantially center between the light emitting element 52 and the light receiving element 54. The optimum distance W1 is a distance which approximately doubles a depth D of the blood vessel 7. For example, if the depth D is about 3 mm, the optimum distance W1 is about 5 mm to 6 mm.

Therefore, in the blood vessel type irradiation/light reception position selection process, a blood vessel type relative position condition employs that "the blood vessel 7 is located at a center between an irradiation position and a measurement light reception position, and a distance between the irradiation position and the measurement light reception position is the same as the predetermined optimum distance W1", light emitting elements 52 and light receiving elements 54 satisfying the blood vessel type relative position condition are searched for, and an irradiation position and a measurement light reception position for use in the blood vessel type are selected. In the first embodiment, for example, as illustrated in FIG. 6, a nearly central position in a length direction of each selected blood vessel portion 7b is set as a measurement point P11, a light emitting element 52 satisfying the blood vessel type relative position condition is set as a measurement light emitting element 52-1, and a light receiving element 54 satisfying the condition is set as a measurement light receiving element 54-1.

In a case where there are no light emitting element 52 and light receiving element 54 satisfying the blood vessel type relative position condition at the set measurement point P11, a light emitting element 52 and a light receiving element 54 satisfying the blood vessel type relative position condition are searched for again after the measurement point P11 is shifted by a predetermined unit distance along the central line L11. In a case where positions satisfying the condition are not found yet, the process is repeatedly performed in the same manner, and the irradiation position and the measurement light reception position are selected.

On the other hand, in the "non-blood vessel type", as illustrated in FIG. 7B, if a light emitting element 52 and a light receiving element 54 are selected at the optimum distance W2 shorter than the optimum distance W1 in the "blood vessel type", reaching depth of measurement light is smaller than the depth D of the blood vessel 7, and a propagation range of the measurement light does not reach the blood vessel 7. Therefore, blood vessel transmitted light is not received by the light receiving element 54, and it is possible to receive only non-blood vessel part transmitted light which has been transmitted through the dermal layer which is a non-blood vessel part located further toward the skin surface than the blood vessel 7.

Therefore, in the non-blood vessel type irradiation/light reception position selection process, a non-blood vessel type relative position condition employs that "the blood vessel 7 is located at a center between an irradiation position and a measurement light reception position and a distance between the irradiation position and the measurement light reception position is the same as the optimum distance W2", a light emitting element 52 and a light receiving element 54 satisfying the non-blood vessel type relative position condition are searched for, and an irradiation position and a measurement light reception position for use in the non-blood vessel type are selected. For example, as illustrated in FIG. 6, at each measurement point P11 which is set in the blood vessel portion through the blood vessel type irradiation/light reception position selection process, a light emitting element 52 satisfying the non-blood vessel type relative position condition is set as a measurement light emitting element 52-2, and a light receiving element 54 satisfying the condition is set as a measurement light receiving element 54-2. The optimum distance W2 is set in advance in accordance with a reaching depth (a depth from the skin surface of the dermal layer) suitable to measure tissue fluid.

In the "non-blood vessel type", the measurement may be performed so as to avoid the blood vessel 7. Therefore, the invention is not limited to a case where the measurement point P11 is set on the blood vessel 7 as illustrated in FIG. 6. For example, a measurement point may be separately set in the white region of FIG. 6 where there is no blood vessel 7 under the skin, and an irradiation position and a measurement light reception position may be selected.

Then, a blood glucose level is measured by selectively using the "blood vessel type" or the "non-blood vessel type" on the basis of a body motion of the subject 2. In the "blood vessel type" measurement, measurement light is applied from all irradiation positions (the measurement light emitting elements 52-1) for use in the blood vessel type, and then a blood vessel transmitted light component is extracted from a light reception result in each measurement light reception position (the measurement light receiving element 54-1) for use in the blood vessel type. On the other hand, in the "non-blood vessel type" measurement, measurement light is applied from all irradiation positions (the measurement light emitting elements 52-2) for use in the non-blood vessel type, and then a non-blood vessel part transmitted light component is extracted from a light reception result in each measurement light reception position (the measurement light receiving element 54-2) for use in the non-blood vessel type. In this case, for example, a wavelength of light emitted by the light emitting element 52 is changed so that a wavelength λ of measurement light is changed within a near infrared region, and thus an optical spectrum (absorption spectrum) of blood vessel transmitted light or non-blood vessel part transmitted light is generated for each wavelength λ. Then, a blood glucose level is calculated (estimated) on the basis of the absorption spectrum by using a "calibration curve" indicating a relationship between a predefined glucose concentration in blood or tissue fluid and an absorbance. In addition, as a technique for generating an absorption spectrum and calculating a concentration of a predetermined component (for example, a glucose concentration) on the basis of the absorption spectrum, a well-known technique may be employed as appropriate. Through the process here, a plurality of measured values can be obtained with one measurement.

In addition, measurement procedures are not particularly limited, and there may be a configuration in which all combinations of the light emitting elements 52 and the light receiving elements 54 are sequentially selected, and then measurements are performed.

Functional Configuration

Figure 8:
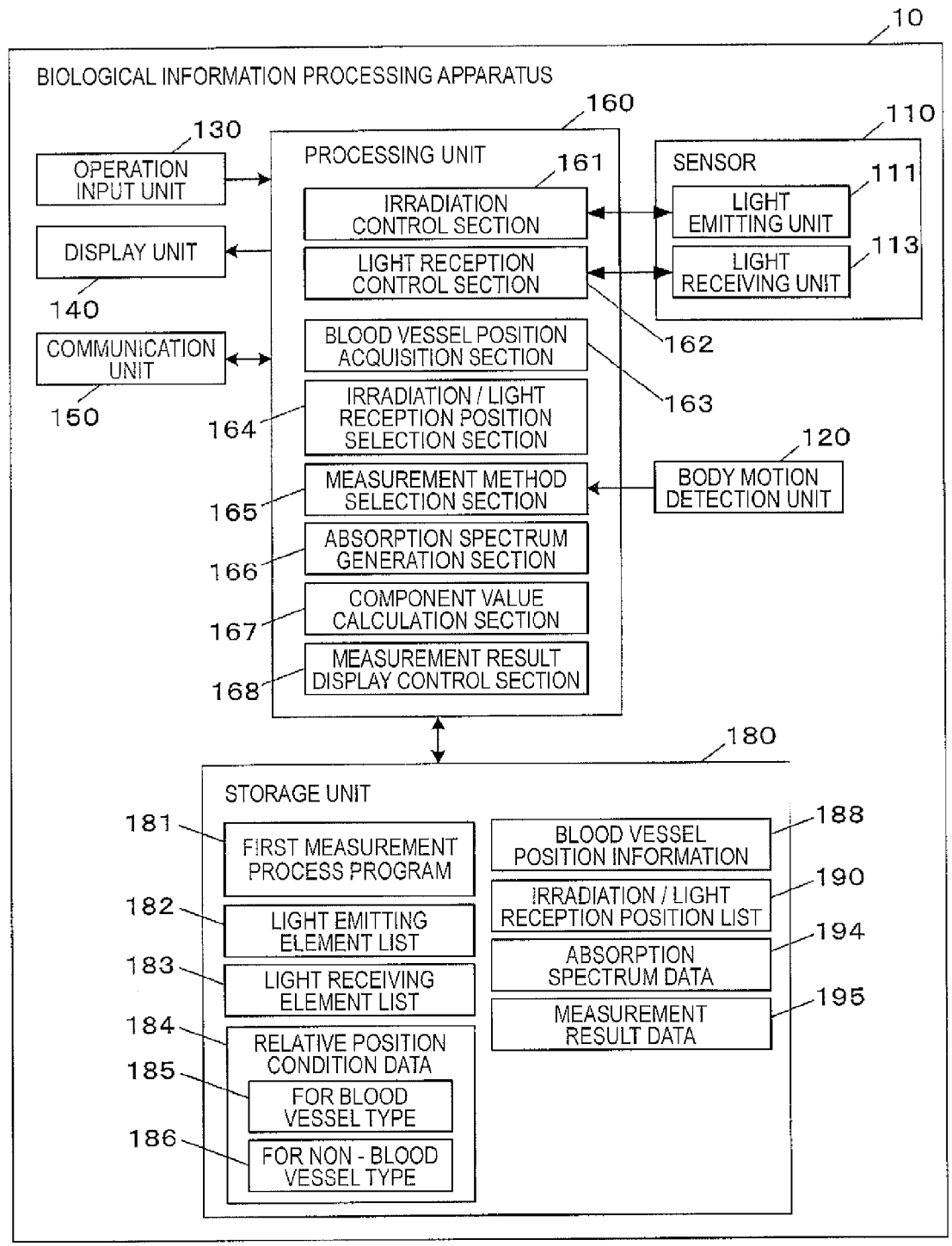
FIG. 8 is a block diagram illustrating a functional configuration example of a biological information processing apparatus in a first embodiment.

FIG. 8 is a block diagram illustrating a main functional configuration example of the biological information processing apparatus 10 in the first embodiment. As illustrated in FIG. 8, the biological information processing apparatus 10 includes a sensor 110, a body motion detection unit 120, an operation input unit 130, a display unit 140, a communication unit 150, a processing unit 160, and a storage unit 180.

The sensor 110 corresponds to the sensor module 50 of FIGS. 2A and 2B, and includes a light emitting unit 111 constituted by a plurality of light emitting elements 52 and a light receiving unit 113 constituted by a plurality of light receiving elements 54. An arrangement position (Xs-Ys coordinate value) of each of the light emitting elements 52 forming the light emitting unit 111 is stored in advance as a light emitting element list 182 correlated with a light emitting element number assigned to a corresponding light emitting element 52 in the storage unit 180. In addition, an arrangement position (Xs-Ys coordinate value) of each of the light receiving elements 54 forming the light receiving unit 113 is stored in advance as a light receiving element list 183 correlated with a light receiving element number assigned to a corresponding light receiving element 54 in the storage unit 180.

The body motion detection unit 120 detects a body motion, and may be implemented by using, for example, microelectromechanical systems (MEMS) sensor. The acceleration sensor 60 of FIG. 1 corresponds to the body motion detection unit 120, and outputs detected acceleration to the processing unit 160 at any time.

The operation input unit 130 is implemented by using an input device such as various switches including a button switch or a dial switch, or a touch panel, and outputs an operation input signal corresponding to an operation performed by a user to the processing unit 160. The operation switch 16 and the touch panel 18 of FIG. 1 correspond to the operation input unit 130. The display unit 140 is implemented by using a display device such as a liquid crystal display (LCD) or an electroluminescence (EL) display, and displays various screens on the basis of display signals from the processing unit 160. The touch panel 18 of FIG. 1 corresponds to the display unit 140.

The communication unit 150 is a communication device which transmits and receives information used in the apparatus to and from an external information processing apparatus under the control of the processing unit 160. The communication device 20 of FIG. 1 corresponds to the communication unit 150. As a communication method of the communication unit 150, various types may be employed, such as a form in which wired connection is made via a cable conforming to a predetermined communication standard, a form in which connection is made via an intermediate device which is also used as a charger called a cradle, a form in which wireless connection is made by using wireless communication.

The processing unit 160 is implemented by a microprocessor such as a central processing unit (CPU) or a digital signal processor (DSP), and a control device and a calculation device such as an application specific integrated circuit (ASIC), and collectively controls the respective units of the biological information processing apparatus 10. The control board 30 of FIG. 1 corresponds to the processing unit 160. The processing unit 160 includes an irradiation control section 161, a light reception control section 162, a blood vessel position acquisition section 163, an irradiation/light reception position selection section 164, a measurement method selection section 165 as a selection section, an absorption spectrum generation section 166, a component value calculation section 167, and a measurement result display control section 168 as a display control section. In addition, the respective sections forming the processing unit 160 may be constituted by hardware such as dedicated module circuits.

The irradiation control section 161 individually light emission of the light emitting elements 52 forming the light emitting unit 111. For example, the control may be realized by using a so-called active matrix driving control technique. The light reception control section 162 performs control for outputting an electric signal corresponding to an intensity of light received by the light receiving elements 54 of the light receiving unit 113.

The blood vessel position acquisition section 163 acquires a biological image (refer to FIG. 4) of a tissue under the skin covered with the sensor module 50, acquires a blood vessel position by performing an image process on the biological image, and selects a blood vessel portion suitable for a measurement. The acquisition of the blood vessel position is performed by using a technique of capturing a biological image in a well-known vein authentication technique or the like, or by using a technique for identifying a vein pattern from a biological image in the well-known vein authentication technique or the like, as appropriate.

The irradiation/light reception position selection section 164 performs a blood vessel type irradiation/light reception position selection process for use in the "blood vessel type". In other words, the irradiation/light reception position selection section 164 sets a measurement point in each selected blood vessel portion, and searches for a light emitting element 52 and a light receiving element 54 satisfying the blood vessel type relative position condition so as to select an irradiation position (the measurement light emitting element 52-1) and a measurement light reception position (the measurement light receiving element 54-1). On the other hand, the irradiation/light reception position selection section 164 performs a non-blood vessel type irradiation/light reception position selection process for use in the "non-blood vessel type". In other words, the irradiation/light reception position selection section 164 selects an irradiation position (the measurement light emitting element 52-2) and a measurement light reception position (the measurement light receiving element 54-2) at each measurement point set at the blood vessel portion. Data regarding the blood vessel type relative position condition including the optimum distance W1 is stored as data for the blood vessel type 185, and data regarding the non-blood vessel type relative position condition including the optimum distance W2 is stored as data regarding the non-blood vessel type 186, and the two data items are stored in advance as relative position condition data 184 in the storage unit 180.

Figure 9:
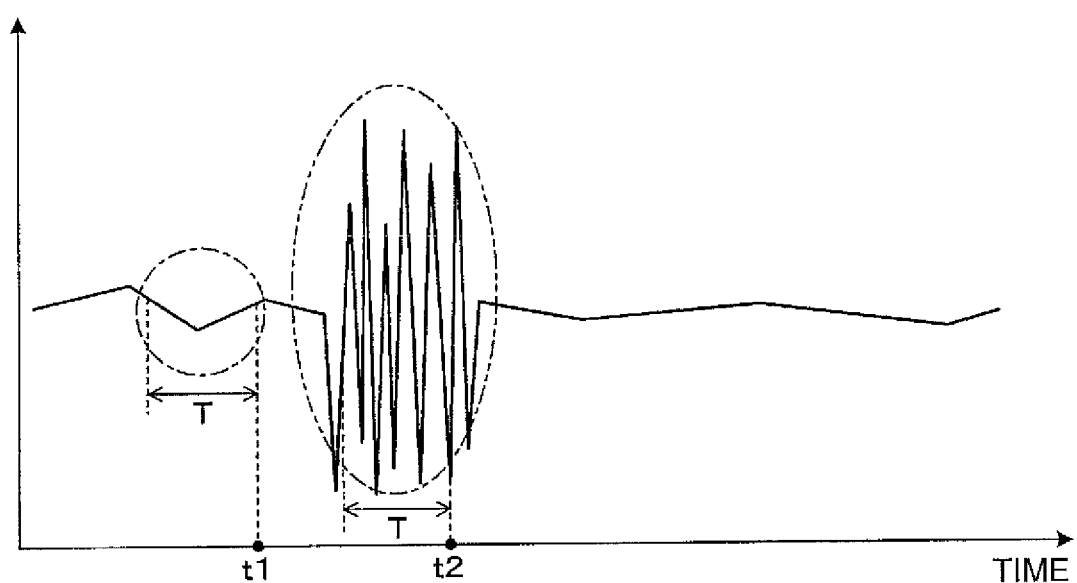
FIG. 9 is a diagram for explaining a determination of a level of a body motion.

The measurement method selection section 165 determines a level of a body motion of the subject 2 on the basis of detected acceleration which is output from the body motion detection unit 120 at any time, and selects the "blood vessel type" in a case where a level of the body motion is low, and "non-blood vessel type" in a case where a level of the body motion is high, as an applied measurement method. FIG. 9 is a diagram illustrating a determination of a level of a body motion. The measurement method selection section 165 obtains a variance value of detected acceleration, for example, for preceding T seconds, and determines that a level of a body motion is low if "the variance value of detected acceleration for the preceding T seconds is smaller than a predetermined threshold value". In addition, if "the variance value of detected acceleration for the preceding T seconds is equal to or greater than the predetermined threshold value", it is determined that a level of the body motion is high.

For example, at a certain time point t1, a variation in detected acceleration for preceding T seconds surrounded and indicated by a dot chain line in FIG. 9 is small, and a variance value decreases. In this case, it is determined that a level of a body motion is low. In contrast, at the time point t2, detected acceleration for preceding T seconds surrounded and indicated by a two-dot chain line in FIG. 9 gradually greatly varies, and a variance value increases. In this case, it is determined that a level of a body motion is high.

In addition, not only a variance value but also amplitude (a difference between the maximum value and the minimum value of detected acceleration for preceding T seconds) of detected acceleration may be obtained, and a level of a body motion may be determined through a threshold value process. Further, under a condition in which a level of a body motion is low if "a ratio (number) of pieces of detected acceleration smaller than a predetermined value is equal to or larger than a predetermined threshold value among pieces of detected acceleration output from the body motion detection unit 120 for preceding T seconds", it is determined whether or not a level of a body motion is low. On the other hand, under a condition in which a level of a body motion is high if "a ratio of pieces of detected acceleration larger than a predetermined value is equal to or larger than a predetermined threshold value among pieces of detected acceleration output from the body motion detection unit 120 for preceding T seconds", it is determined whether or not a level of a body motion is high. The absorption spectrum generation section 166 applies measurement light from the measurement light emitting element 52-1 or the measurement light emitting element 52-2 of each measurement point set as an irradiation position, under the control of the irradiation control section 161 and the light reception control section 162. The absorption spectrum generation section 166 generates an absorption spectrum on the basis of a light reception result obtained by the measurement light receiving element 54-1 or the measurement light receiving element 54-2 of each measurement point set as a measurement light reception position.

The component value calculation section 167 calculates a glucose concentration in blood or tissue fluid, which is an aimed component on the basis of the absorption spectrum. For example, a blood glucose level is calculated from the absorption spectrum by using an analysis method such as a multiple regression analysis method, a main component regression analysis method, a PLS regression analysis method, or an independent component analysis method.

The measurement result display control section 168 performs control for displaying the blood glucose level calculated by the component value calculation section 167 on the display unit 140 as a measurement result.

The storage unit 180 is implemented by using various integrated circuit (IC) memories such as a read only memory (ROM), a flash ROM, or a random access memory (RAM) or a hard disk. The storage unit 180 stores a program for operating the biological information processing apparatus 10 and realizing various functions of the biological information processing apparatus 10, data used during execution of the program, or the like, in advance, or temporarily stores data each time a process is performed. In FIG. 1, the main memory 34 or the measurement data memory 36 mounted on the control board 30, and the memory card 22 correspond to the storage unit 180.

The storage unit 180 stores in advance a first measurement process program 181, the light emitting element list 182, the light receiving element list 183, and the relative position condition data 184. The first measurement process program 181 causes the processing unit 160 to function as the irradiation control section 161, the light reception control section 162, the blood vessel position acquisition section 163, the irradiation/light reception position selection section 164, the measurement method selection section 165, the absorption spectrum generation section 166, the component value calculation section 167, and the measurement result display control section 168, so as to perform a first measurement process (refer to FIG. 11).

In addition, the storage unit 180 stores blood vessel position information 188, an irradiation/light reception position list 190, absorption spectrum data 194, and measurement result data 195 when a measurement is performed.

The irradiation/light reception position list 190 stores an irradiation position and a measurement light reception position selected as a result of the blood vessel type irradiation/light reception position selection process for use in the blood vessel type, and stores an irradiation position and a measurement light reception position selected as a result of the non-blood vessel type irradiation/light reception position selection process for use in the non-blood vessel type. FIG. 10 is a diagram illustrating a data configuration example of the irradiation/light reception position list 190. As illustrated in FIG. 10, the irradiation/light reception position list 190 is a data table in which an irradiation position and a measurement light reception position for use in the blood vessel type 192 and an irradiation position and a measurement light reception position for use in the non-blood vessel type 193 are set in correlation with a measurement point number 191. A light emitting element number of a corresponding light emitting element 52, that is, the measurement light emitting element 52-1 is registered in the irradiation position for use in the blood vessel type 192, and a light receiving element number of a corresponding light receiving element 54, that is, the measurement light receiving element 54-1 is registered in the measurement light reception position. A light emitting element number of a corresponding light emitting element 52, that is, the measurement light emitting element 52-2 is registered in the irradiation position for use in the non-blood vessel type 193, and a light receiving element number of a corresponding light receiving element 54, that is, the measurement light receiving element 54-2 is registered in the measurement light reception position.

Flow of Process

Figure 11:
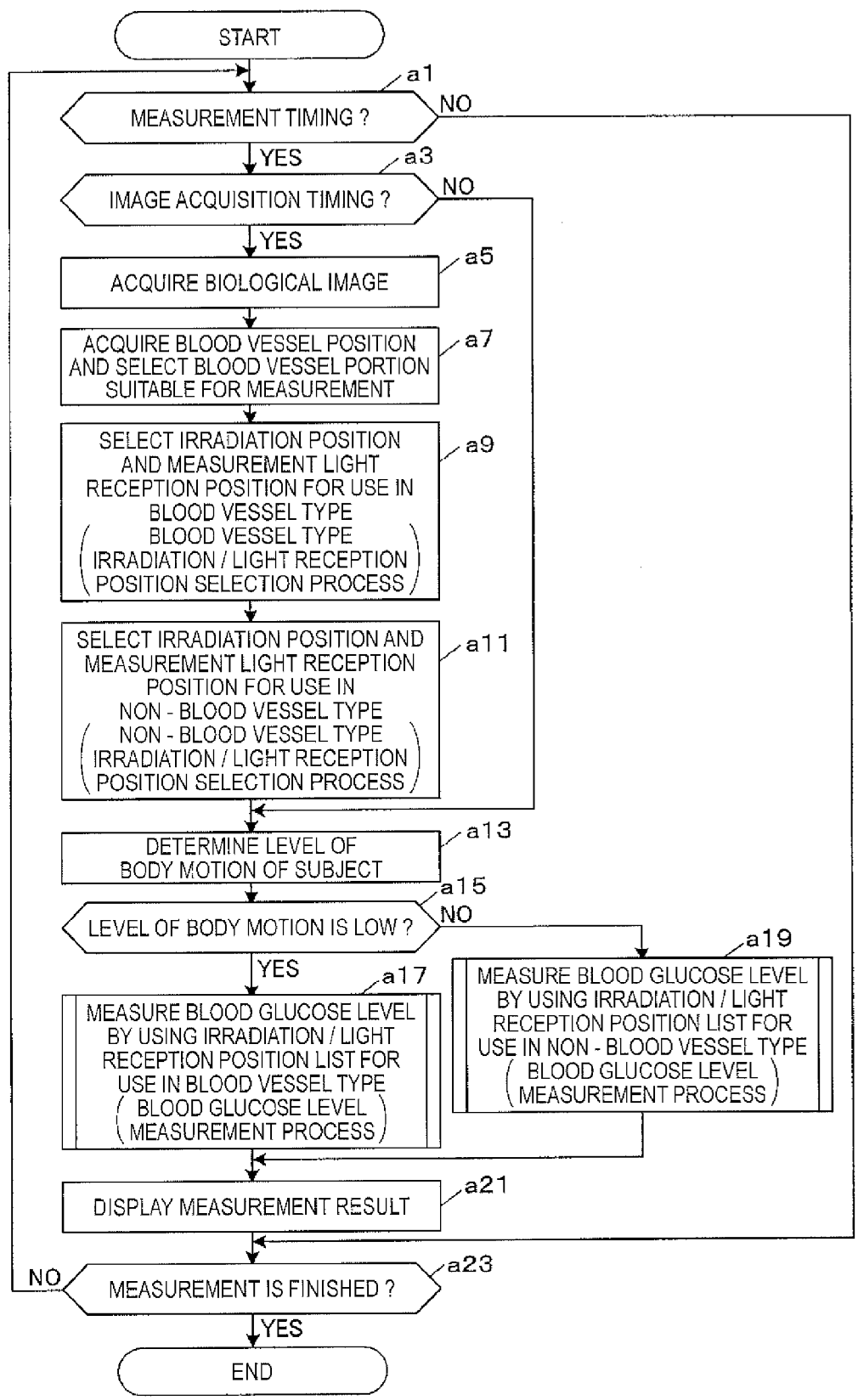
FIG. 11 is a flowchart illustrating process procedures of a first measurement process.

FIG. 11 is a flowchart illustrating process procedures of the first measurement process. The process described here may be performed by the processing unit 160 reading and executing the first measurement process program 181 from the storage unit 180. The first measurement process is started when the biological information processing apparatus 10 is mounted on the body of the subject 2, and a predetermined measurement start operation is input thereto.

As illustrated in FIG. 11, in the first measurement process, first, a standby state occurs until a measurement time arrives (step a1: NO). For example, in a case where a measurement is performed every one minute, the time at which one minute has elapsed from the previous measurement timing is determined as a measurement timing (step a1: YES), and then it is determined whether or not an image acquisition timing arrives. If it is determined that the image acquisition timing arrives (step a3: YES), the flow proceeds to step a5. If the image acquisition timing does not arrives (step a3: NO), the flow proceeds to step a13. Here, the image acquisition timing may be, for example, ten minutes, and may be one hour, but if biological images are frequently captured at short intervals and blood vessel positions are acquired, measurement accuracy can be maintained. In contrast, as the interval is set to become longer, power consumption can be reduced. However, in a case where a blood vessel position under the skin does not match an acquired blood vessel position or a blood vessel cannot be accurately specified due to a mounting location of the sensor module 50 being deviated, a measurement cannot be accurately performed until the next blood vessel position is acquired. The image acquisition timing is appropriately set in consideration of this situation.

In step a5, the irradiation control section 161 causes the light emitting elements 52 of the sensor module 50 to simultaneously emit light, and the light reception control section 162 causes all the light receiving elements 54 to receive light (an image is captured), so that a biological image is acquired. Next, the blood vessel position acquisition section 163 performs an image process on the biological image so as to acquire a blood vessel position which is viewed from the skin surface, and selects a blood vessel portion (step a7). For example, the blood vessel position acquisition section 163 performs a binarization or a filtering process on each pixel of the acquired biological image (luminance image) through comparison with reference luminance, so as to acquire a blood vessel position. A pixel having luminance lower than the reference luminance indicates a blood vessel. In addition, the blood vessel position acquisition section 163 excludes accuracy reducing factor portions, and selects a blood vessel portion having a length which is equal to or larger than the predetermined smallest site length. The acquired blood vessel position or a position of the selected blood vessel portion is stored as the blood vessel position information 188 in the storage unit 180.

Next, the irradiation/light reception position selection section 164 performs the blood vessel type irradiation/light reception position selection process so as to set a measurement point for each blood vessel portion and to select an irradiation position and a measurement light reception position for use in the blood vessel type (step a9). In addition, the irradiation/light reception position selection section 164 performs the non-blood vessel type irradiation/light reception position selection process so as to select an irradiation position and a measurement light reception position for use in the non-blood vessel type for each measurement point set in step a9 (step S11). At this time, the irradiation/light reception position selection section 164 assigns a measurement point number 191 to each measurement point, and generates the irradiation/light reception position list 190 by correlating a light emitting element number of the measurement light emitting element 52-1 and a light receiving element number of the measurement light receiving element 54-1 with the blood vessel type 192 and correlating a light emitting element number of the measurement light emitting element 52-2 and a light receiving element number of the measurement light receiving element 54-2 with the non-blood vessel type 193.

In step a13, the measurement method selection section 165 determines a level of a body motion of the subject 2 on the basis of detected acceleration from the body motion detection unit 120. If it is determined that a level of the body motion is low in this process (step a15: YES), a blood glucose level measurement process is performed by using the data for use in the blood vessel type 192 of the irradiation/light reception position list 190 (step a17). Then, the flow proceeds to step a21. On the other hand, if it is determined that a level of the body motion is high (step a15: NO), a blood glucose level measurement process is performed by using the data for use in the non-blood vessel type 193 of the irradiation/light reception position list 190 (step a19). After the blood glucose level measurement process is performed, the flow proceeds to step a21.

Figure 12:
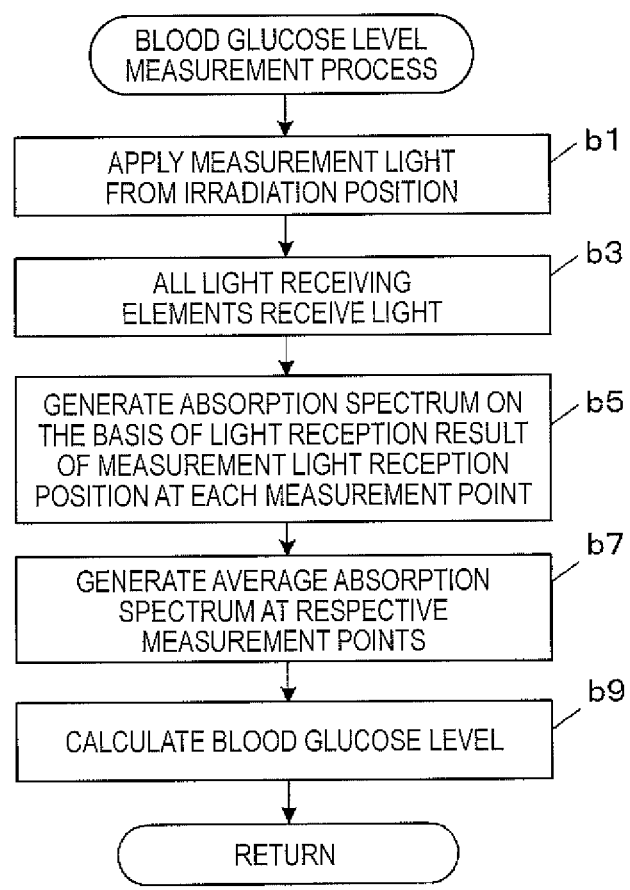
FIG. 12 is a flowchart illustrating specific process procedures of a blood glucose level measurement process.

FIG. 12 is a flowchart illustrating specific process procedures of the blood glucose level measurement process. As illustrated in FIG. 12, in the blood glucose level measurement process, the irradiation control section 161 causes the irradiation positions to simultaneously emit light according to the irradiation/light reception position list 190 (step b1), and the light reception control section 162 causes all the light receiving elements 54 to receive light (step b3). Next, the absorption spectrum generation section 166 generates an absorption spectrum on the basis of light reception results at corresponding measurement light reception positions at respective measurement points (step b5), and generates an average absorption spectrum by averaging the generated absorption spectra at the respective measurement points (step b7). The spectrum data regarding the generated average absorption spectrum is stored as the absorption spectrum data 194 in the storage unit 180. The component value calculation section 167 calculates a blood glucose level on the basis of the average absorption spectrum generated in step b7 (step b9). The calculated blood glucose level is stored as the measurement result data 195 in the storage unit 180.

In step a21, the measurement result display control section 168 refers to the measurement result data 195 and performs control for displaying the blood glucose level calculated through the blood glucose level calculation process in step a17 or a19 on the display unit 140 as a measurement result. Then, the flow returns to step a1 and the above-described processes are repeatedly performed until the measurement is finished (step a23: NO).

As described above, according to the first embodiment, a body motion of the subject 2 is detected, and if a level of the body motion is low, it is possible to perform a measurement using the "blood vessel type" which has high measurement accuracy but is easily influenced by the body motion of the subject 2. On the other hand, if a level of the body motion of the subject 2 is high, it is possible to perform a measurement using the "non-blood vessel type" which has lower measurement accuracy than that of the "blood vessel type" but is scarcely influenced by the body motion of the subject 2. Therefore, it is possible to prevent a situation in which measurement accuracy is considerably reduced due to a body motion, or a measurement cannot be performed so that an effective measurement result cannot be obtained, and thus to stably provide a measurement result. For example, even in a case of measuring a blood glucose level of a diabetic, it is possible to continuously monitor a blood glucose level.

Second Embodiment

A second embodiment is fundamentally realized in the same manner as the first embodiment, but is different therefrom in that a "blood vessel type" measurement and a "non-blood vessel type" measurement are performed together as a measurement method.

Figure 13:
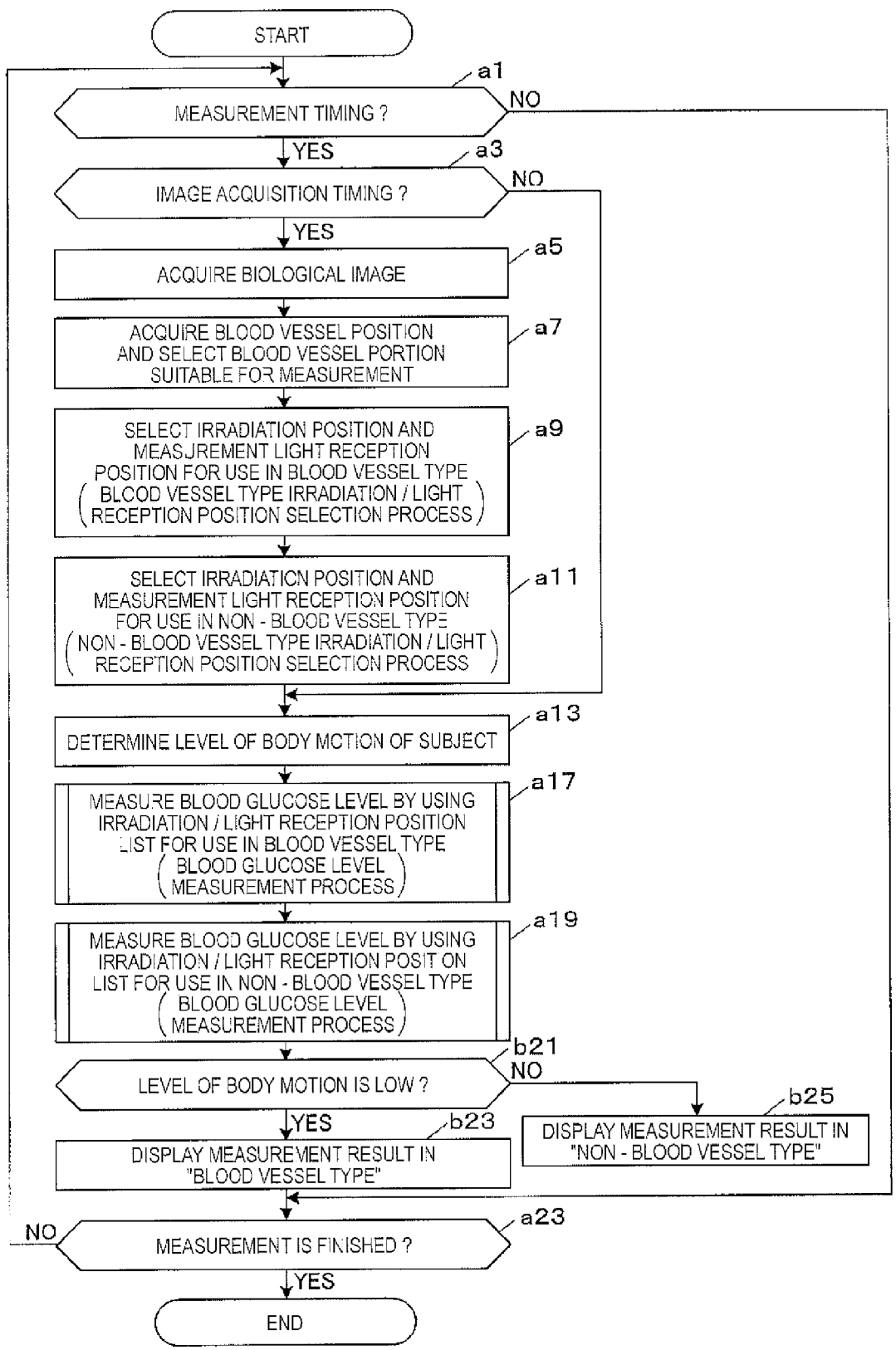
FIG. 13 is a flowchart illustrating process procedures of a second measurement process.

FIG. 13 is a flowchart illustrating a flow (second measurement process) of a process performed by the processing unit 160 in the second embodiment. The second embodiment may be realized by storing a second measurement process program for realizing the second measurement process in the storage unit 180 instead of the first measurement process program 181 in the biological information processing apparatus 10 of the first embodiment illustrated in FIG. 8. In FIG. 13, the same process steps as in the first embodiment are given the same reference numerals. As illustrated in FIG. 13, in the measurement process of the second embodiment, after a level of a body motion of the subject 2 is determined in step a13, a blood glucose level measurement process is performed by using the data for use in the blood vessel type 192 of the irradiation/light reception position list 190 (step a17), and a blood glucose level measurement process is performed by using the data for use in the non-blood vessel type 193 of the irradiation/light reception position list 190 (step a19).

Then, the process is made to branch out depending on whether or not a level of the body motion is determined as being low in step a13, and if it is determined that a level of the body motion is low (step b21: YES), the measurement result display control section 168 displays a measurement result in the "blood vessel type" performed in step a17 (step b23). On the other hand, if a level of the body motion is high (step b21: NO), the measurement result display control section 168 refers to the measurement result data 195 and displays a measurement result in the "non-blood vessel type" performed in step a19 (step b25).

As described above, according to the second embodiment, the "blood vessel type" measurement and the "non-blood vessel type" measurement are performed together, and it is possible to selectively display a measurement result in the "blood vessel type" if a level of a body motion of the subject 2 is low and a measurement result in the "non-blood vessel type" if a level of the body motion is high.

Third Embodiment

In a third embodiment, for example, only a "blood vessel type" measurement is performed, and the time related to duration (measurement time) for applying measurement light in a single measurement, which is one of parameters used for the measurement, is set on the basis of a detection result of a body motion of the subject 2. The same portions as in the above-described respective embodiments are given the same reference numerals.

In the third embodiment, if a level of a body motion of the subject 2 is low, a measurement time is set to be long. If the measurement time is lengthened, and exposure is performed for a long period of time, an S/N ratio can be increased, and thus a measurement can be performed with higher accuracy.

The measurement time is set in advance to, for example, time which is sufficient to achieve the highest accuracy which can be realized.

In contrast, in a case where a level of a body motion of the subject 2 is high, if the measurement time is long, a blood vessel position may be moved during exposure, and thus a measurement may not be accurately performed. Therefore, if a level of the body motion is high, the measurement time is set to be short, and thus a probability that a blood vessel may be deviated from a target during a measurement (for the measurement time) is reduced. If the blood vessel is not deviated from the target during exposure, the blood vessel can be measured as a measurement object site, and, even if the blood vessel is deviated therefrom, only a non-blood vessel part can be measured unless the deviation occurs for the measurement time. Since whether or not the blood vessel is deviated from the target can be determined by analyzing an absorption spectrum, if it is determined that the blood vessel is deviated, a blood glucose level may be calculated by using a "calibration curve" indicating a glucose concentration in tissue fluid and an absorbance in a subsequent process.

Functional Configuration

Figure 14:
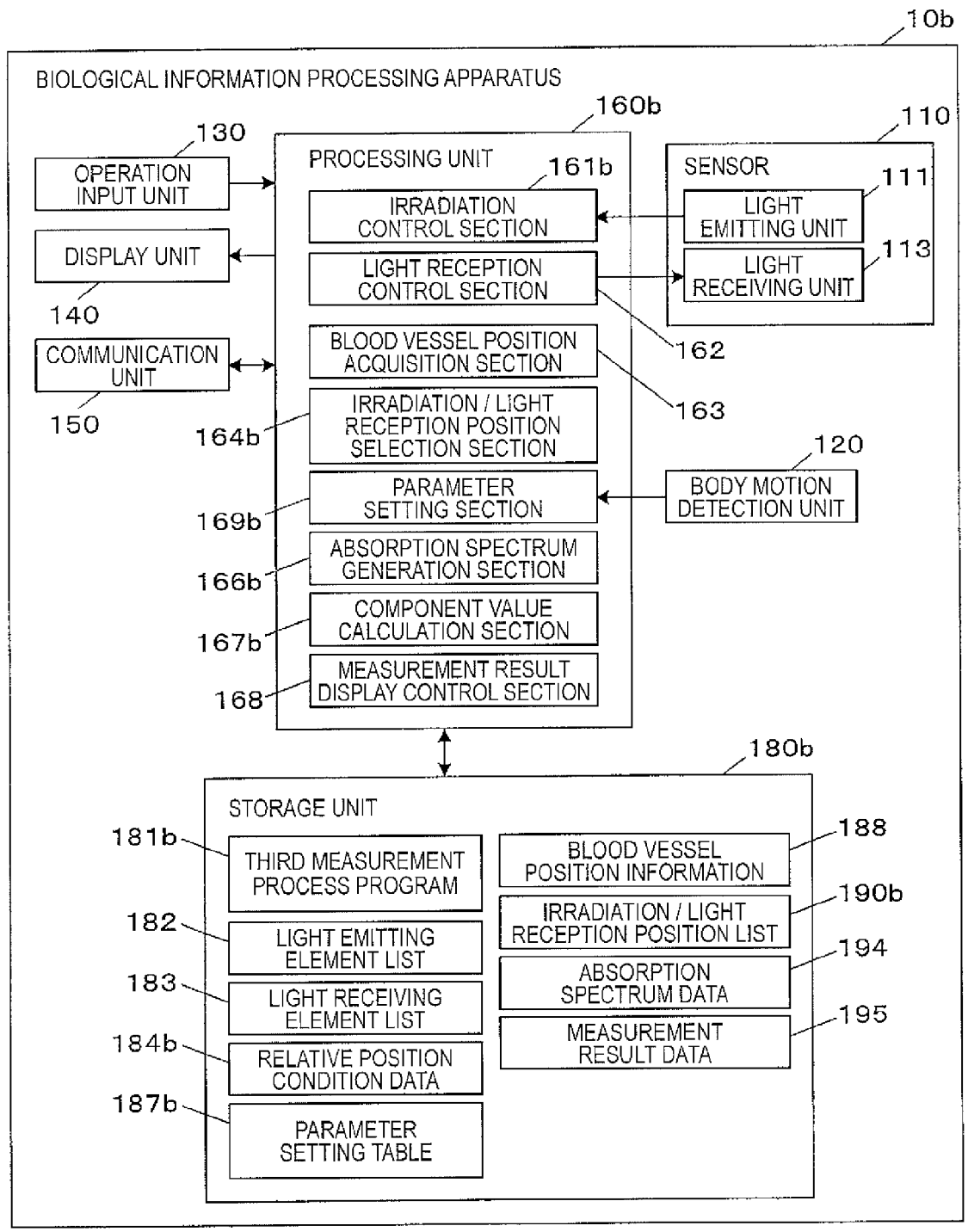
FIG. 14 is a block diagram illustrating a functional configuration example of a biological information processing apparatus in a third embodiment.

FIG. 14 is a block diagram illustrating a main functional configuration example of a biological information processing apparatus 10*b* in the third embodiment. As illustrated in FIG. 14, the blood glucose level measurement apparatus 10*b* includes a sensor 110, a body motion detection unit 120, an operation input unit 130, a display unit 140, a communication unit 150, a processing unit 160*b*, and a storage unit 180*b*.

In the third embodiment, the processing unit 160*b* includes an irradiation control section 161*b*, a light reception control section 162, a blood vessel position acquisition section 163, an irradiation/light reception position selection section 164*b*, a parameter setting section 169*b*, an absorption spectrum generation section 166*b*, a component value calculation section 167*b*, and a measurement result display control section 168. In the third embodiment, only a "blood vessel type" measurement is performed, and thus each functional section is different from that of the first embodiment in that only a process related to the "blood vessel type" measurement is performed.

In other words, the irradiation/light reception position selection section 164*b* performs a blood vessel type irradiation/light reception position selection process. Data regarding the blood vessel type relative position condition is stored in advance as relative position condition data 184*b* in the storage unit 180*b*. The absorption spectrum generation section 166*b* applies measurement light from the measurement light emitting element 52-1 of each measurement point set as an irradiation position, under the control of the irradiation control section 161*b* and the light reception control section 162*b*, so as to generate an absorption spectrum on the basis of a light reception result obtained by the measurement light receiving element 54-1 of each measurement point set as a measurement light reception position. The component value calculation section 167*b* calculates a glucose concentration in blood for each measurement point on the basis of the absorption spectrum.

The parameter setting section 169*b* determines a level of a body motion of the subject 2 on the basis of detected acceleration which is output from the body motion detection unit 120 at any time, and sets a measurement time according to a parameter setting table 187*b*.

The storage unit 180*b* stores in advance a third measurement process program 181*b*, the light emitting element list 182, the light receiving element list 183, the relative position condition data 184, and the parameter setting table 187*b*. The third measurement process program 181*b* causes the processing unit 160*b* to function as the irradiation control section 161*b*, the light reception control section 162, the blood vessel position acquisition section 163, the irradiation/light reception position selection section 164*b*, the parameter setting section 169*b*, the absorption spectrum generation section 166*b*, the component value calculation section 167*b*, and the measurement result display control section 168, so as to perform a third measurement process (refer to FIG. 16).

The parameter setting table 187*b* stores a measurement time corresponding to a level of a body motion of the subject 2. FIG. 15 is a diagram illustrating a data configuration example of the parameter setting table 187*b*. As illustrated in FIG. 15, in the parameter setting table 187*b*, a measurement time T11 is set if a level of a body motion is low, and a measurement time T13 is set if a level of the body motion is high. A specific value of each of the measurement times T11 and T13 is set in advance in the above-described manner, but at least the measurement time T11 is set to be longer (to a greater value) than the measurement time T13.

In addition, the storage unit 180*b* stores blood vessel position information 188, an irradiation/light reception position list 190*b*, absorption spectrum data 194, and measurement result data 195 when a measurement is performed. Only the data for use in the blood vessel type 192 as illustrated in FIG. 10 is set in the irradiation/light reception position list 190*b*.

Flow of Process

Figure 16:
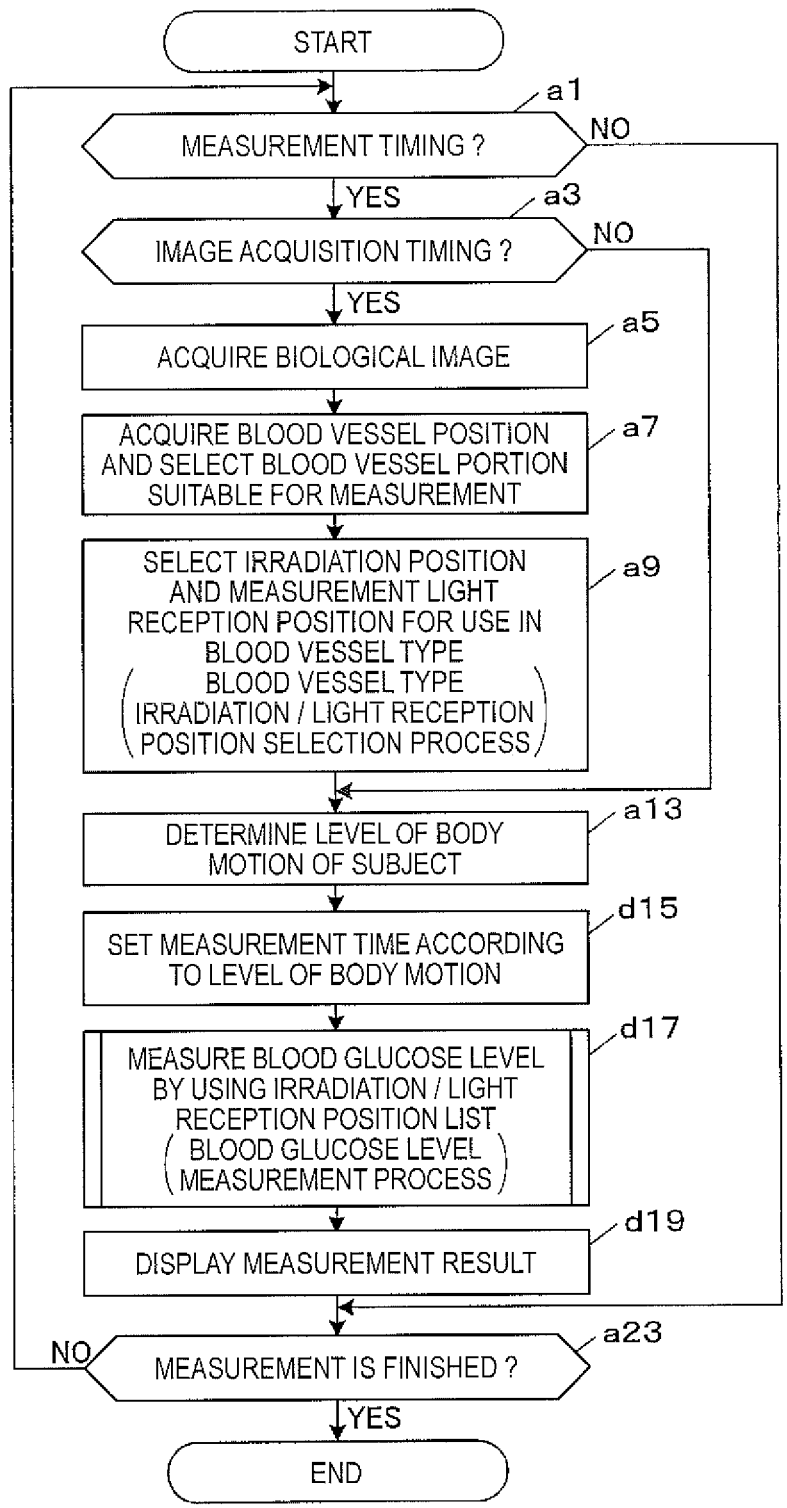
FIG. 16 is a flowchart illustrating process procedures of a third measurement process.

FIG. 16 is a flowchart illustrating process procedures of the third measurement process. The process described here may be performed by the processing unit 160*b* reading and executing the third measurement process program 181*b* from the storage unit 180*b*.

As illustrated in FIG. 16, in the third measurement process, after a level of a body motion of the subject 2 is determined in step a13, the parameter setting section 169*b* refers to the parameter setting table 187*b* and sets a measurement time according to a level of the body motion (step d15). Through the process here, the measurement time is set to be long if a level of the body motion is low, and is set to be short if a level of the body motion is high.

In the subsequent step d17, a blood glucose level measurement process is performed by using the irradiation/light reception position list 190*b*. The blood glucose level measurement process here may be realized in the same procedures as the blood glucose level measurement process (refer to FIG. 12) described in the first embodiment, and, in this case, in step b1 of FIG. 12, the irradiation control section 161*b* causes the irradiation positions to simultaneously emit light with the measurement time set in step d15 as a light emission time.

Then, the measurement result display control section 168 refers to the measurement result data 195 and performs control for displaying the blood glucose level calculated through the blood glucose level calculation process of step d17 on the display unit 140 as a measurement result (step d19).

As described above, according to the third embodiment, if a level of a body motion of the subject 2 is low, a measurement time can be set to be long, and if a level thereof is high, a measurement time can be set to be short. Therefore, it is possible to increase measurement accuracy if a level of the body motion is low. On the other hand, if a level of the body motion is high, it is possible to prevent a situation in which a blood vessel is deviated from a target due to a body motion during a measurement (for a measurement time) and thus measurement accuracy is considerably reduced. Therefore, it is possible to stably provide a measurement result.

In the third embodiment, a measurement time is set in two stages of whether a level of a body motion is low or high, but a width of variance values is finely divided into three or more stages, and a measurement time may be set to be lengthened in stages as a level of a body motion increases.

In the third embodiment, a "blood vessel type" measurement is performed, and a measurement time is set on the basis of a detection result of a body motion of the subject 2. In contrast, a measurement parameter such as the number of measurements may be set in addition to the measurement time. For example, if a level of a body motion is low, a measurement time is set to be long, and the number of measurements is set to one. On the other hand, if a level of the body motion is high, the measurement time is set to be short, and the number of measurements is set to a predetermined number which is equal to or larger than two.

In the present modification example, in a case where a level of a body motion is high, and the number of measurements is a predetermined number, in the blood glucose level calculation process performed in step d17 of FIG. 16, the irradiation control section 161b performs a predetermined number of processes of causing the irradiation positions to simultaneously emit light for the measurement time which is set to be short as the process in step b1 of FIG. 12. In addition, instead of step b5, the next process is performed. In other words, first, absorption spectra obtained in the predetermined number of respective measurements are analyzed, and absorption spectra in which a blood vessel is not deviated from a target (that is, which includes a blood vessel transmitted light component) are selected. Next, an absorption spectrum is generated by averaging the selected absorption spectra for each measurement point. Therefore, an average absorption spectrum is generated (step b7).

According to the present modification example, if a level of a body motion is high, two or more measurements can be performed for a short measurement time. If the measurement time is short, an S/N ratio is small, but, as in the present modification example, if two or more measurements are performed, a blood glucose level can be calculated by selecting an absorption spectrum in which a blood vessel is not deviated from a target, and thus it is possible to improve measurement accuracy.

In the present modification example, both a measurement time and the number of measurements are employed, but only the number of measurements may be used.

In the third embodiment, only a "blood vessel type" measurement is performed, but the content of the third embodiment may be applied to the first and second embodiments in which a "blood vessel type" measurement and a "non-blood vessel type" measurement are performed. In this case, a measurement time is correlated with each of the "blood vessel type" and the "non-blood vessel type". In a case where a "blood vessel type" measurement is performed, the measurement time corresponding to the "blood vessel type" may be selected, and, in a case where a "non-blood vessel type" measurement is performed, the measurement time corresponding to the "non-blood vessel type" may be selected. Of course, a plurality of measurement times may be defined depending on levels of a body motion as a measurement time corresponding to the "blood vessel type", and, in a case where a "blood vessel type" measurement is performed, the measurement time corresponding to a level of a body motion at that time may be selected. This is also the same for a case where a plurality of measurement times corresponding to the "non-blood vessel type" are defined.

In the above-described third embodiment, only a "blood vessel type" measurement is performed, but even in the same "blood vessel type" measurement, measurement times are different, and thus it can be said that the measurement is a different measurement method. In other words, if a measurement performed for a first measurement time is a first measurement method, and a measurement performed for a second measurement time is a second measurement method, a measurement method is defined with a measurement time as a reference, and a measurement performed in a different measurement time may be interpreted as a different measurement method.

Fourth Embodiment

In a fourth embodiment, only a "blood vessel type" measurement is performed in the same manner as in the third embodiment, and the number of measurement points which is one of measurement parameters is set on the basis of a detection result of a body motion of the subject 2. The same portions as in the above-described respective embodiments are given the same reference numerals.

In the fourth embodiment, the number of measurement points is larger in a case where a level of a body motion of the subject 2 is high than in a case where a level thereof is low. In order to perform this, in the fourth embodiment, a measurement point candidate setting process is performed prior to a measurement, so as to set measurement point candidates.

Figure 17:
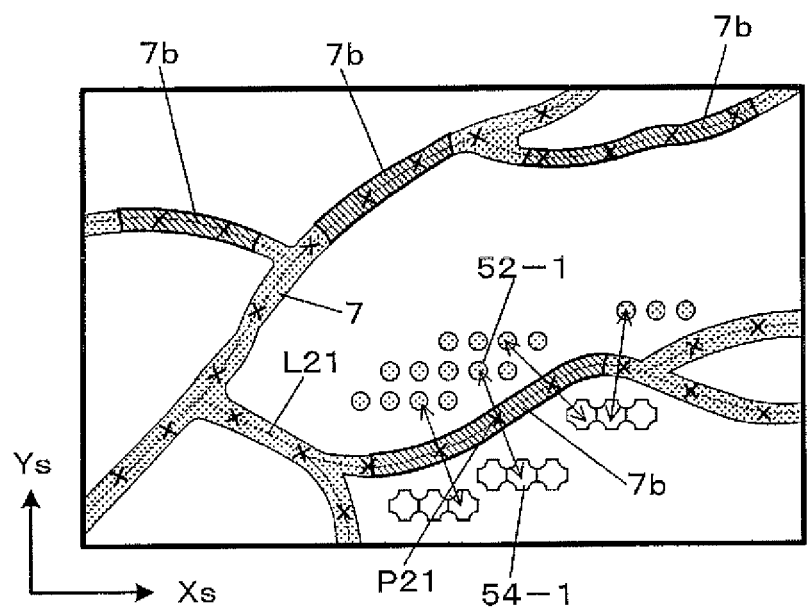
FIG. 17 is a diagram illustrating a measurement point candidate setting process.

FIG. 17 is a diagram for explaining the measurement point candidate setting process. In the measurement point candidate setting process, first, measurement point candidates are temporarily set along the blood vessel 7. For example, as indicated by an "X" mark in FIG. 17, measurement point candidates are temporarily set at predetermined intervals on a central line L21 of the blood vessel 7. A light emitting element 52 and a light receiving element 54 satisfying the blood vessel type relative position condition for each temporarily set measurement point candidate are searched for, and if there are elements satisfying the conditions, the light emitting element 52 is set as a measurement light emitting element 52-1, and the light receiving element 54 is set as a measurement light receiving element 54-1. Through this measurement point candidate setting process, a plurality of measurement point candidates P21 are set in which the light emitting elements 52 and the light receiving elements 54 satisfying the blood vessel type relative position condition are present, and an irradiation position and a measurement light reception position are selected for each of the measurement point candidates P21.

In addition, during the measurement, the number of measurement points is set on the basis of a detection result of a body motion of the subject 2, and the measurement point candidates P21 corresponding to the set number of measurement points are selected as measurement points. At this time, among the measurement point candidates P21, the measurement point candidates P21 which belong to the blood vessel portion 7b which is selected by the blood vessel position acquisition section 163 and is suitable for the measurement are preferentially selected.

As long as a blood vessel is not deviated from a target, a measurement can be performed with high accuracy even if the number of measurement points is increased. As described in the first embodiment, the accuracy reducing factor portions are excluded, and then a measurement point is selected from the blood vessel portion which has the predetermined smallest site length or larger and is thus selected, measurement accuracy can be improved. On the other hand, if a level of the body motion is high, there is a case where a blood vessel position is moved and thus a measurement cannot be accurately performed. However, if the number of measurement points is increased, it is possible to increase a probability that a measurement point remains at which the blood vessel is not deviated from a target among the measurement points.

Functional Configuration

Figure 18:
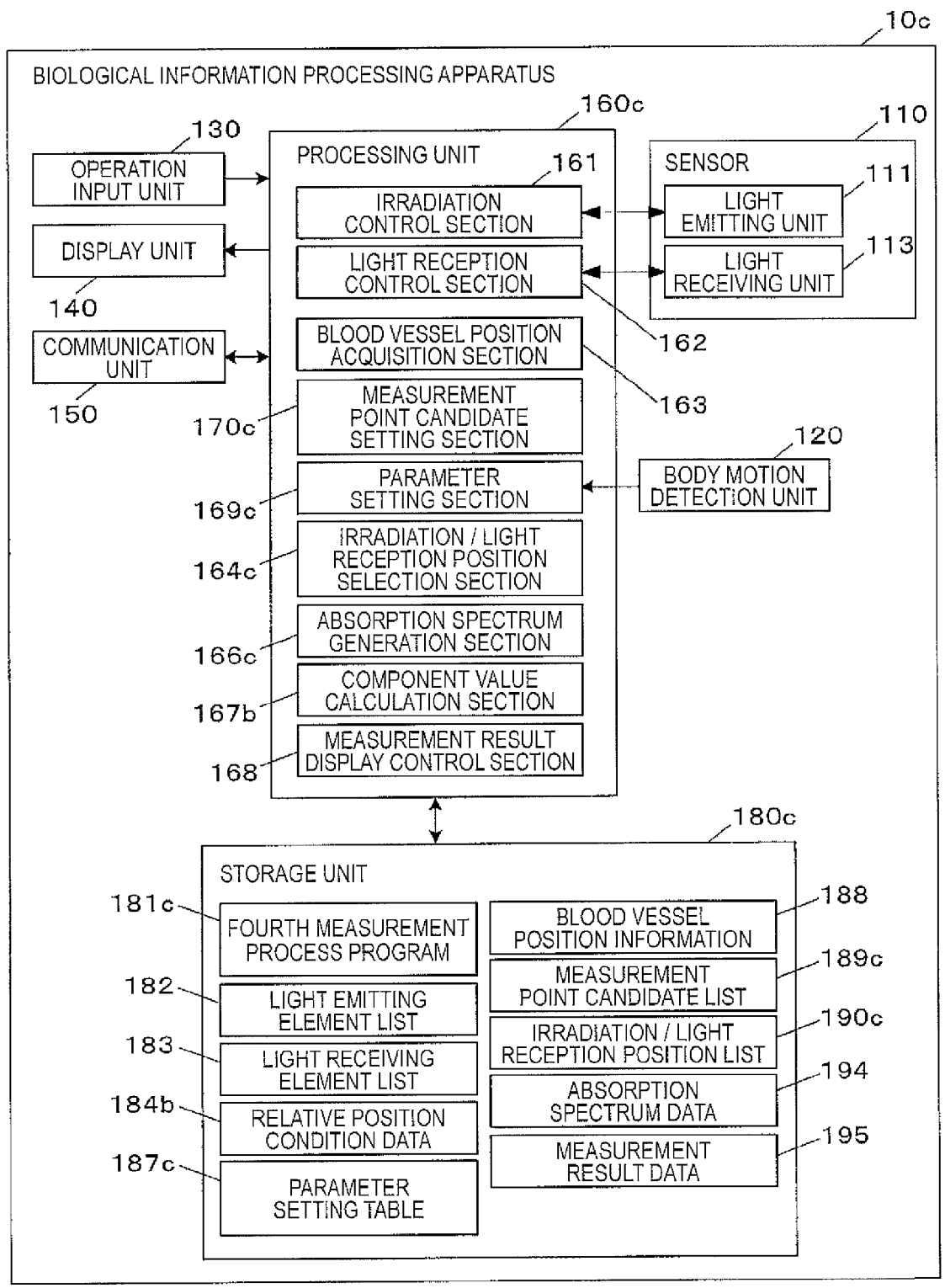
FIG. 18 is a block diagram illustrating a functional configuration example of a biological information processing apparatus in a fourth embodiment.

FIG. 18 is a block diagram illustrating a main functional configuration example of a biological information processing apparatus 10c in the fourth embodiment. As illustrated in FIG. 18, the blood glucose level measurement apparatus 10c includes a sensor 110, a body motion detection unit 120, an operation input unit 130, a display unit 140, a communication unit 150, a processing unit 160c, and a storage unit 180c.

In the fourth embodiment, the processing unit 160c includes an irradiation control section 161, a light reception control section 162, a blood vessel position acquisition section 163, a measurement point candidate setting section 170c, a parameter setting section 169c, an irradiation/light reception position selection section 164c, an absorption spectrum generation section 166c, a component value calculation section 167b, and a measurement result display control section 168.

The measurement point candidate setting section 170c, which is a functional section which performs a measurement point candidate setting process, searches for a light emitting element 52 and a light receiving element 54 satisfying the blood vessel type relative position condition for each measurement point temporality set along a blood vessel so as to set a plurality of measurement point candidates on the blood vessel, and selects an irradiation position (the measurement light emitting element 52-1) and a measurement light reception position (measurement light receiving element 54-1).

The parameter setting section 169c determines a level of a body motion of the subject 2 on the basis of detected acceleration which is output from the body motion detection unit 120 at any time, and sets the number of measurement points according to a parameter setting table 187c.

The storage unit 180c stores in advance a fourth measurement process program 181c, the light emitting element list 182, the light receiving element list 183, the relative position condition data 184b, and the parameter setting table 187c. The fourth measurement process program 181c causes the processing unit 160c to function as the irradiation control section 161, the light reception control section 162, the blood vessel position acquisition section 163, the measurement point candidate setting section 170c, the irradiation/light reception position selection section 164c, the parameter setting section 169c, the absorption spectrum generation section 166b, the component value calculation section 167b, and the measurement result display control section 168, so as to perform a fourth measurement process (refer to FIG. 21). The parameter setting table 187c stores the number of measurement points corresponding to a level of a body motion of the subject 2. FIG. 19 is a diagram illustrating a data configuration example of the parameter setting table 187c. As illustrated in FIG. 19, the number of measurement points is set for each width of variance values which are divided into four stages in the parameter setting table 187c. A specific value of each number of measurement points is not particularly limited, but as a variance value increases, the number of measurement points is set to be increased in stages.

In addition, the storage unit 180c stores blood vessel position information 188, a measurement point candidate list 189c, an irradiation/light reception position list 190c, absorption spectrum data 194, and measurement result data 195 when a measurement is performed.

The measurement point candidate list 189c stores an irradiation position and a measurement light reception position which is selected as a result of the measurement point candidate setting process. FIG. 20 is a diagram illustrating a data configuration example of the measurement point candidate list 189c. As illustrated in FIG. 20, the measurement point candidate list 189c is a data table in which an irradiation position and a measurement light reception position selected for a corresponding measurement point candidate, and a priority flag are set in correlation with a measurement point candidate number. As the priority flag, "ON" is set for a measurement point candidate which belongs to a blood vessel portion suitable for a measurement, and "OFF" is set for a measurement point candidate which does not belong thereto.

Flow of Process

Figure 21:
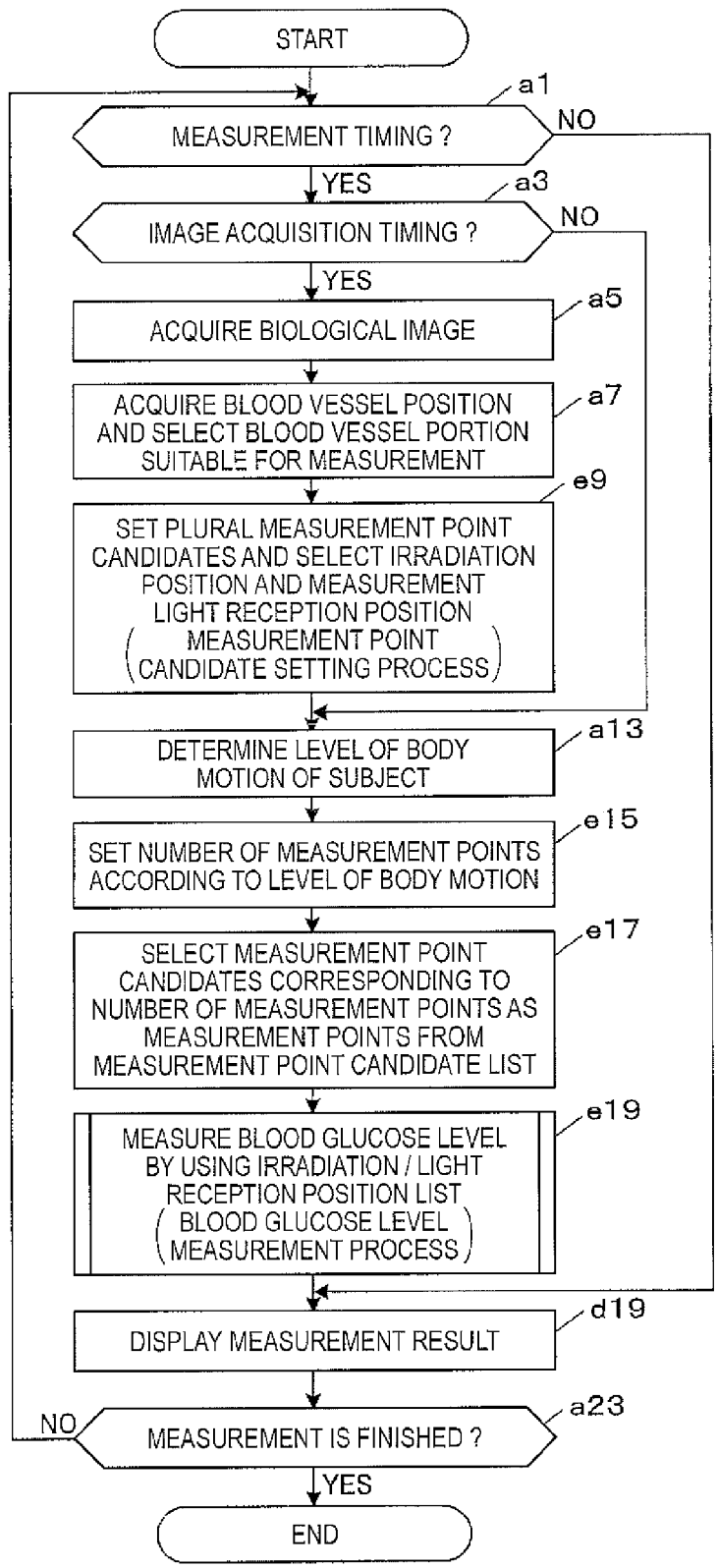
FIG. 21 is a flowchart illustrating process procedures of a fourth measurement process.

FIG. 21 is a flowchart illustrating process procedures of the fourth measurement process. The process described here may be performed by the processing unit 160c reading and executing the fourth measurement process program 181c from the storage unit 180c.

As illustrated in FIG. 21, in the fourth measurement process, after a blood vessel portion is selected in step a7, the measurement point candidate setting section 170c performs a measurement point candidate setting process so as to set a plurality of measurement point candidates on a blood vessel, and selects an irradiation position and a measurement light reception position (step e9). At this time, the measurement point candidate setting section 170c assigns a measurement point candidate number to each measurement point candidate. A priority flag of a measurement point candidate which belongs to the blood vessel portion selected in the previous step a7 is set to "ON", and a priority flag of a measurement point candidate which does not belongs to the blood vessel portion selected in the previous step a7 is set to "OFF". The priority flag is correlated with a light emitting element number of the measurement light emitting element 52-1 and a light receiving element number of the measurement light receiving element 54-1 so that the measurement point candidate list 189c is generated. After a level of a body motion of the subject 2 is determined in step a13, the parameter setting section 169c refers to the parameter setting table 187c and sets number of measurement points according to a level of the body motion (step e15). Through the process here, the number of measurement points is set to be small if a level of the body motion is low, and is set to be large if a level of the body motion is high.

Next, the irradiation/light reception position selection section 164c refers to the measurement point candidate list 189c, and sequentially selects measurement point candidates corresponding to the number of measurement points set in step e15 as measurement points from among the measurement point candidates which have the priority flag of "ON" (step e17).

At this time, the irradiation/light reception position selection section 164c assigns a measurement point number to the selected measurement point, and correlates the measurement point number with the irradiation position and the measurement light reception position set in the measurement point candidate list 189c, so as to generate the irradiation/light reception position list 190c.

Then, a blood glucose level measurement process is performed by using the irradiation/light reception position list 190c (step e19). The blood glucose level measurement process here may be realized in the same procedures as the blood glucose level measurement process (refer to FIG. 12) described in the first embodiment, and, in this case, in step b7 of FIG. 12, the absorption spectrum generation section 166c analyzes absorption spectra obtained in the predetermined number of respective measurements, and selects absorption spectra in which a blood vessel is not deviated from a target (that is, which includes a blood vessel transmitted light component) so as to further generate an average absorption spectrum.

As described above, according to the fourth embodiment, the number of measurement points is set to be larger in a case where a level of a body motion of the subject 2 is high than in a case where a level thereof is low. Therefore, while maintaining measurement accuracy if a level of a body motion is low, it is possible to prevent a situation in which a blood vessel is deviated from a target due to a body motion and thus measurement accuracy is considerably reduced if a level of the body motion is high. Therefore, it is possible to stably provide a measurement result.

In the fourth embodiment, only a "blood vessel type" measurement is performed, but the content of the fourth embodiment may be applied to the first and second embodiments in which a "blood vessel type" measurement and a "non-blood vessel type" measurement are performed. In this case, the parameter setting table 187c is set for each of the "blood vessel type" and the "non-blood vessel type". In a case where a "blood vessel type" measurement is performed, the parameter setting table 187c corresponding to the "blood vessel type" may be selected, and, in a case where a "non-blood vessel type" measurement is performed, the parameter setting table 187c corresponding to the "non-blood vessel type" may be selected. In the above-described fourth embodiment, only a "blood vessel type" measurement is performed, but even in the same "blood vessel type" measurement, number of measurement points is different, and thus it can be said that the measurement is a different measurement method. In other words, if a measurement performed in a first number of measurement points is a first measurement method, and a measurement performed in a second number of measurement points is a second measurement method, a measurement method is defined with the number of measurement points as a reference, and a measurement performed in a different number of measurement points may be interpreted as a different measurement method.

Through a combination of the above-described third embodiment and fourth embodiment, both a measurement time and the number of measurement points may be set on the basis of a detection result of a body motion of the subject 2. Alternatively, the number of measurements may be further set in addition to the measurement time and the number of measurement points.

In the above-described embodiments, a case has been described in which the biological information processing apparatus 10 mainly measures a blood glucose level as a blood component, but the biological information processing apparatus 10 is also applicable to a case where other blood components are measured. For example, the present embodiment is applicable to measurements of levels of enzymes such as glutamic pyruvic transaminase (GPT), levels of proteins in blood plasma such as albumin, cholesterol levels, or lactic acid values.

In addition, the invention is also applicable to a case of measuring a living tissue state as biological information of the subject 2. For example, the invention is also applicable to a case where ultrasonic waves are applied toward a living body of a subject as irradiation waves and a blood vessel diameter is measured as a living tissue state, or a case where blood pressure is measured (estimated) on the basis of blood vessel diameter changes.

What is claimed is:

1. A biological information processing apparatus comprising:
    a body motion detection unit that detects a motion of a body of a subject;
    a selection unit that selects one measurement method based upon a result of the detection by the body motion detection unit, the one measurement method being selected from among a plurality of measurement methods of measuring a blood component by applying irradiation waves toward the body of the subject; and
    a display control unit that performs control for displaying a measurement result obtained by performing a measurement according to the one measurement method,
    wherein the plurality of measurement methods are different from each other and depend on measurement object sites, and
    wherein, when the detection result satisfies a condition indicating that a level of the body motion is above a threshold, the selection unit selects one measurement method in which a non-blood vessel portion other than a blood vessel is set as the measurement object site.

2. The biological information processing apparatus according to claim 1, further comprising:
    a parameter setting unit that sets a measurement parameter related to the one measurement method based upon the detection result.

3. The biological information processing apparatus according to claim 2, wherein the parameter setting unit sets (1) at least one of a number of measurement points, and (2) a measurement time corresponding to a duration in which the irradiation waves are applied, as the measurement parameter.

4. The biological information processing apparatus according to claim 1, wherein, when the detection result satisfies a condition indicating that a level of the body motion is below a threshold, the selection unit selects one measurement method in which a blood vessel portion is set as the measurement object site.

5. The biological information processing apparatus according to claim 1, further comprising:
    a measurement unit that measures the blood component by using the plurality of measurement methods together,
    wherein the display control unit displays a measurement result that is obtained by performing a measurement according to the one measurement method among measurement results from the measurement unit.

6. The biological information processing apparatus according to claim 1, wherein the measurement methods are a plurality of methods for measuring a blood glucose level.

7. A biological information processing method comprising:
    detecting a motion of a body of a subject;
    selecting one measurement method based upon a result of the detection, the one measurement method being selected from among a plurality of measurement methods of measuring a blood component by applying irradiation waves toward the body of the subject; and performing control for displaying a measurement result obtained by performing a measurement according to the one measurement method, wherein the plurality of measurement methods are different from each other and depend on measurement object sites, and wherein, when the detection result satisfies a condition indicating that a level of the body motion is above a threshold, selecting one measurement method in which a non-blood vessel portion other than a blood vessel is set as the measurement object site.

8. A biological information processing apparatus comprising:

a wearable sensor adapted to detect a characteristic of a subject;

a processor configured to execute a step of selecting a measurement method for measuring a blood component based upon the detected characteristic, and a step of measuring the blood component using the selected measurement method, wherein the measurement method is selected from among a plurality of measurement methods that measure the blood component by using irradiation waves; and a display that displays a result of a measurement obtained by the processor, wherein the plurality of measurement methods are different from each other and depend on measurement object sites, and wherein, when the detection of the characteristic satisfies a condition indicating that a level of the body motion is above a threshold, the processor is configured to execute a step of selecting one measurement method in which a non-blood vessel portion other than a blood vessel is set as the measurement object site.

* * * * *